(12) United States Patent
Wilson

(10) Patent No.: US 10,702,577 B2
(45) Date of Patent: *Jul. 7, 2020

(54) COMBINATION THERAPIES USING CYCLOSPORINE AND AROMATIC CATIONIC PEPTIDES

(71) Applicant: STEALTH BIOTHERAPEUTICS CORP, Monaco (MC)

(72) Inventor: D. Travis Wilson, Newton, MA (US)

(73) Assignee: STEALTH BIOTHERAPEUTICS CORP, Monaco (MC)

( * ) Notice: Subject to any disclaimer, the term of this patent is extended or adjusted under 35 U.S.C. 154(b) by 0 days.

This patent is subject to a terminal disclaimer.

(21) Appl. No.: 15/397,030

(22) Filed: Jan. 3, 2017

(65) Prior Publication Data

US 2017/0319647 A1    Nov. 9, 2017

Related U.S. Application Data

(63) Continuation of application No. 14/185,471, filed on Feb. 20, 2014, now Pat. No. 9,561,258, which is a continuation of application No. 13/634,192, filed as application No. PCT/US2011/028543 on Mar. 15, 2011, now Pat. No. 8,697,657.

(60) Provisional application No. 61/313,945, filed on Mar. 15, 2010, provisional application No. 61/376,813, filed on Aug. 25, 2010.

(51) Int. Cl.
| | |
|---|---|
| *A61K 38/07* | (2006.01) |
| *A61K 38/13* | (2006.01) |
| *A61K 38/06* | (2006.01) |
| *A61K 38/08* | (2019.01) |

(52) U.S. Cl.
CPC .............. *A61K 38/13* (2013.01); *A61K 38/06* (2013.01); *A61K 38/07* (2013.01); *A61K 38/08* (2013.01)

(58) Field of Classification Search
None
See application file for complete search history.

(56) References Cited

U.S. PATENT DOCUMENTS

| | | | |
|---|---|---|---|
| 4,522,811 A | 6/1985 | Eppstein et al. | |
| 5,674,534 A | 10/1997 | Zale et al. | |
| 5,716,644 A | 2/1998 | Zale et al. | |
| 5,760,001 A | 6/1998 | Girten et al. | |
| 6,468,798 B1 | 10/2002 | Debs et al. | |
| 6,593,292 B1 * | 7/2003 | Rothbard | A61K 49/0043 514/1.2 |
| 7,550,439 B2 | 6/2009 | Szeto | |
| 7,781,405 B2 | 8/2010 | Szeto | |
| 8,697,657 B2 * | 4/2014 | Wilson | A61K 38/06 514/21.9 |
| 9,561,258 B2 * | 2/2017 | Wilson | A61K 38/06 |
| 2004/0248808 A1 | 12/2004 | Szeto et al. | |
| 2006/0084606 A1 | 4/2006 | Szeto | |
| 2008/0182797 A1 | 7/2008 | Nudler et al. | |
| 2009/0298747 A1 | 12/2009 | Shapiro | |
| 2009/0317402 A1 | 12/2009 | Rajpal et al. | |
| 2012/0329730 A1 | 12/2012 | Szeto et al. | |
| 2013/0059784 A1 | 3/2013 | Wilson | |

FOREIGN PATENT DOCUMENTS

| | | |
|---|---|---|
| JP | 11-504617 | 4/1999 |
| JP | 2007-518818 | 7/2007 |
| JP | 2007-532507 A | 11/2007 |
| WO | WO-96/22104 A1 | 7/1996 |
| WO | WO-96/40073 | 12/1996 |
| WO | WO-99/15154 | 4/1999 |
| WO | WO-00/38651 | 7/2000 |
| WO | WO-2004/070054 A2 | 8/2004 |
| WO | WO-2009/108695 A2 | 9/2009 |
| WO | WO-2010/076329 A1 | 7/2010 |
| WO | WO-2011/025734 | 3/2011 |
| WO | WO-2011/082328 A1 | 7/2011 |

OTHER PUBLICATIONS

Kang, 2000, Journal of Drug Targeting, 8:6, 425-434 (Year: 2000).*
Non-Final Office Action on U.S. Appl. No. 14/910,440 dated Dec. 28, 2017.
Amselem et al., "A Large-Scale Method for the Preparationof Sterile and Nonpyrogenic Liposomal Formulations of Defined Size Distributions for Clinical Use," CRC Press, 1993, pp. 501-525.
Baffy, György, "Kupffer cells in non-alcoholic fatty liver disease: The emerging view," J. Hepatol. (Jul. 1, 2009), vol. 51, No. 1, pp. 212-223.
Bassuk et al., "Non-selective cyclooxygenase inhibition before periodic acceleration (pGz) cardiopulmonary resuscitation (CPR) in a porcine model of ventricular fibrillation." Resuscitation. 77(2):250-7 (2008).
Chonn and Cullis, "Recent Advances in Liposome Drug Delivery Systems," Current Opinion in Biotechnology 6:698-708 (1995).
Extended European Search Report issued for Application No. 11756870.9 dated Sep. 5, 2013 (19 pages).
Extended European Search Report dated May 9, 2016, in EP Application No. 15187915.2 (20 pages).
Extended Search Report received in European Patent Application No. 14163505.2 dated Mar. 3, 2015, 22 pages.
Gabriel, Thomas, "Simple, Rapid Method for Converting a Peptide From One Salt Form to Another," Int. J. Peptide Protein Res., (1987), vol. 30, pp. 40-43.

(Continued)

*Primary Examiner* — Satyanarayana R Gudibande
(74) *Attorney, Agent, or Firm* — Foley & Lardner LLP

(57) ABSTRACT

The invention provides compositions and methods for preventing or treating an ischemia-reperfusion injury, such as occurs during acute myocardial infarction and organ transplant in a mammalian subject. The methods comprise administering to the subject an effective amount of an aromatic-cationic peptide or a pharmaceutically acceptable salt thereof, and one or more additional active agents such as cyclosporine.

14 Claims, No Drawings

(56) References Cited

OTHER PUBLICATIONS

Garcia-Gonzalez, et al., New pharmacologic options in "the treatment of acute coronary syndromes and myocardial ischemia-reperfusion injury: potential role of levosimendan." abstract only Minerva Cardioangiologica. 55(5): 625-35 (2007).
Gregoriadis, "Engineering Liposomes for Drug Delivery: Progress and Problems," Trends Biotechnol., 13(12):527-37 (1995).
Haag, Rainer, "Supramolecular Drug-Delivery Systems Based on Polymeric Core-Shell Architectures," Agnew. Chem. Int. Ed., (2004), vol. 43, pp. 278-282.
Higashi et al., "Edaravone (3-methyl-1-phenyl-2-pyrazolin-5-one), a novel free radical scavenger, for treatment of cardiovascular diseases." Abstract only Recent Patents on Cardiovascular Drug Discovery. 1(1):85-93 (2006).
International Preliminary Report on Patentability (Chapter I) in Application No. PCT/US2011/028543 dated Sep. 27, 2012 (8 pages).
International Preliminary Report on Patentability (Chapter II) issued in PCT/US2011/28543 dated Dec. 14, 2012 (16 pages).
International Search Report and Written Opinion of the International Searching Authority in Application No. PCT/US2011/028543 dated May 19, 2011 (11 pages).
International Search Report and Written Opinion of the International Searching Authority received in Application No. PCT/US2014/050747 dated Dec. 10, 2014, 7 pages.
Kasama et al., "Effects of intravenous atrial natriuretic peptide on cardiac sympathetic nerve activity and left ventricular remodeling in patients with first anterior acute myocardial infarction." Journal of the American College of Cardiology. 49(6):667-74 (2007).
Kennedy et al., "Effect of perhexiline and oxfenicine on myocardial function and metabolism during low-flow ischemia/reperfusion in the isolated rat heart." Journal of Cardiovascular Pharmacology. 36(6): 794-801 (2000).
Kim et al., "Involvement of adrenergic pathways in activation of catalase by myocardial ischemia-reperfusion." American Journal of Physiology—Regulatory Integrative & Comparative Physiology. 282(5):R1450-1458, (2002).
Kingma, J. H. and van Gilst, W. H., "Angiotensin-converting enzyme inhibition during thrombolytic therapy in acute myocardial infarction: the Captopril and Thrombolysis Study (CATS)." Herz. 18 Suppl 1:416-23 (1993).
Kovacs et al., "Prevalent role of Akt and ERK activation in cardioprotective effect of Ca(2 ) channel- and beta-adrenergic receptor blockers." Molecular & Cellular Biochemistry. 321(1-2):155-164 (2009).
Lichtenberg et al., "Liposomes: Preparation, Characterization, and Preservation," Methods Biochem. Anal. 33: 337-462 (1988).
Lishmanov, Yu B. et al., "Role of Opiate Receptors and ATP-Dependent Potassium Channels of Mitochondria in the Formation of Myocardial Adaptive Resistance to the Arrhythmogenic Effect of Ischemia and Reperfusion," Biology Bulletin of the Russian Academy of Sciences, (Nov. 2003), vol. 30, Issue 6, pp. 603-609.
Lucchinetti et al., "Sevoflurane inhalation at sedative concentrations provides endothelial protection against ischemia-reperfusion injury in humans." Anesthesiology. 106(2):262-268 (2007).
Maslov, L.N. et al., "Interaction of peripheral mu-opioid receptors and K(ATP)-channels in regulation of cardiac electrical stability in ischemia, reperfusion, and postinfarction cardiosclerosis," Ross Fiziol Zh Im I M Sechenova, (Jul. 2002), 88(7), pp. 842-850; Abstract Only from Chemical Abstracts Service, Columbus, Ohio, US, (Nov. 21, 2002) (3 pages).
Mizguchi et al., "Intratumor administration of fusogenic liposomes containing fragment A of diphtheria toxin suppresses tumor growth," Cancer Lett. 100: 63-69 (1996).
Moller "(Optimaal) echocardiographic substudy." American Heart Journal. 147(3):494-501 (2004).
Non-Final Office Action on U.S. Appl. No. 14/185,471 dated Feb. 16, 2016.
Non-Final Office Action received in U.S. Appl. No. 13/634,192 dated Mar. 11, 2013 (11 pages).
Notice of Allowance on U.S. Appl. No. 14/185,471 dated Sep. 13, 2016.
Notice of Allowance received for U.S. Appl. No. 13/634,192 dated Nov. 18, 2013 (15 pages).
Ochiai et al., Impact of cilostazol on clinical and angiographic outcome after primary stenting for acute myocardial infarction. American Journal of Cardiology. 84(9):1074-6, A6, A9, (1999).
Office Action received in Japanese Patent Application No. 2013-500162, dated Mar. 16, 2015, 3 pages.
Paprica, P.A. et al., "Preparation of Novel Cyclosporin A Derivatives," Bioconjugate Chem., (1992), vol. 3, pp. 32-36.
Platonov, AA et al., "Delta-opioid receptor agonists prevent the irreversible damage of cardiomyocytes in ischemized-reperfused isolated rat heart," Eksp Klin Farmakol, (Nov.-Dec. 2004), 67(6), pp. 26-29; Abstract Only from Chemical Abstracts Service, Columbus, Ohio, US, (Jan. 28, 2005) (3 pages).
Reddy, Ann. "Controlled-Release, Pegylation, Liposomal Formulations: New Mechanisms in the Delivery of Injectable Drugs," Pharmacother., 34(7-8):915-923 (2000).
Schiller et al., "Synthesis and in vitro opiod activity profiles of DALDA analogues," vol. 335, Issue 10, Oct. 10, 11 pages.
Sikri, N. and Bardia, A., A history of streptokinase use in acute myocardial infarction. Texas Heart Institute Journal. 34(3):318-27 (2007).
Solenkova, NV et al., "Comparative study of the antiarrhythmic activity of mu- and delta-opioid receptor agonists during acute cardiac ischemia and reperfusion models in rats," Eksp Klin Farmakol, (Nov.-Dec. 2005), 68(6), pp. 25-29; Abstract Only from Chemical Abstracts Service, Columbus, Ohio, US (Mar. 5, 2006) (3 pages).
Varas-Lorenzo et al., "Use of oral corticosteroids and the risk of acute myocardial infarction." Atherosclerosis. 192(2): 376-83 (2007).
Viehman et al., "Daltroban, a thromboxane receptor antagonist, protects the myocardium against reperfusion injury following myocardial ischemia without protecting the coronary endothelium." Abstract only Methods & Findings in Experimental & Clinical Pharmacology. 12(10):651-6 (1990).
Weiner, "Liposomes for Protein Delivery: Selecting Manufacture and Development Processes," Immunomethods, 4(3):201-9 (1994).
Wu, Dunli et al., "A highly potent peptide analgesic that protects against ischemia-reperfusion-induced myocardial stunning", Am J Physiol Heart Circ Physiol, (Aug. 2002), vol. 283, No. 2, pp. H783-H791.
Ye et al., "Enhanced cardioprotection against ischemia-reperfusion injury with a dipyridamole and low-dose atorvastatin combination." American Journal of Physiology—Heart & Circulatory Physiology. 293(1):H813-8 (2007).
Yount, Nannette Y. et al., "Selective reciprocity in antimicrobial activity versus cytotoxicity of hBD-2 and crotamine," PNAS, (Sep. 1, 2009), vol. 106, No. 35, pp. 14972-14977.
Zhao et al., "Transcellular Transport of a Highly Polar 3 Net Charge Opioid Tetrapeptide," The Journal of Pharmacology and Experimental Therapeutics, vol. 34, No. 1, 2003, pp. 425-432.
Zhao, Guo-Min et al., "Comparison of [Dmt1]DALDA and DAMGO in Binding and G Protein Activation at μ, δ, and κ Opioid Receptors," J. Parmacology and Experimental Therapeutics, (2003), vol. 307, No. 3, pp. 947-954.
Search Report issued on European Application 17150292.5, dated Jul. 14, 2017.

\* cited by examiner

COMBINATION THERAPIES USING CYCLOSPORINE AND AROMATIC CATIONIC PEPTIDES

CROSS-REFERENCE TO RELATED APPLICATIONS

This application is a continuation of U.S. patent application Ser. No. 14/185,471, filed Feb. 20, 2014, which is a continuation of U.S. patent application Ser. No. 13/634,192, filed Nov. 8, 2012, now U.S. Pat. No. 8,697,657, which is the U.S. National Stage of International Patent Application No. PCT/US2011/028543, filed Mar. 15, 2011, which claims benefit of and priority to U.S. Provisional Patent Application No. 61/313,945, filed Mar. 15, 2010, and U.S. Provisional Patent Application No. 61/376,813, filed Aug. 25, 2010. The contents of these applications are incorporated herein by reference in their entireties.

TECHNICAL FIELD

The present technology relates generally to methods and compositions for preventing or treating organ damage resulting from ischemia and reperfusion. In particular, embodiments, the present technology relates to administering aromatic-cationic peptides in combination with cyclosporine, or other therapeutic agents, in effective amounts to prevent or treat ischemia-reperfusion injury associated with acute myocardial infarction and organ transplantation in mammalian subjects.

SUMMARY

The present technology relates to compositions and methods for the treatment or prevention of ischemia-reperfusion injury associated with acute myocardial infarction and organ transplantation in mammals. In general, the methods and compositions include one or more aromatic-cationic peptides or pharmaceutically acceptable salts thereof (e.g., acetate salt or trifluoroacetate salt) in conjunction with one or more additional active agents. In some embodiments, the aromatic-cationic peptide is one or more aromatic-cationic peptides selected from the group consisting of Tyr-D-Arg-Phe-Lys-NH$_2$; 2',6'-Dmt-D-Arg-Phe-Lys-NH$_2$; Phe-D-Arg-Phe-Lys-NH$_2$; 2',6'-Dmp-D-Arg-Phe-Lys-NH$_2$; and D-Arg-2',6'-Dmt-Lys-Phe-NH$_2$, or a pharmaceutically acceptable salt thereof, such as acetate salt or trifluoroacetate salt. In some embodiments, the peptide comprises D-Arg-2',6'-Dmt-Lys-Phe-NH$_2$ or an acetate salt or trifluoroacetate salt thereof, and the additional active agent includes cyclosporine or a cyclosporine derivative or analogue. In some embodiments, the cyclosporine or a cyclosporine derivative or analogue includes NIM811.

In some aspects, the present technology provides a pharmaceutical composition comprising (i) an aromatic-cationic peptide or a pharmaceutically acceptable salt thereof, and (ii) one or more additional active agents. In some embodiments, the aromatic-cationic peptide is selected from the group consisting of: Tyr-D-Arg-Phe-Lys-NH$_2$; 2',6'-Dmt-D-Arg-Phe-Lys-NH$_2$; Phe-D-Arg-Phe-Lys-NH$_2$; 2',6'-Dmp-D-Arg-Phe-Lys-NH$_2$; and D-Arg-2',6'-Dmt-Lys-Phe-NH$_2$. In some embodiments, the pharmaceutically acceptable salt comprises acetate salt or trifluoroacetate salt. In some embodiments, the additional active agent comprises cyclosporine or a cyclosporine derivative or analogue. In some embodiments, the pharmaceutical composition comprises the D-Arg-2',6'-Dmt-Lys-Phe-NH$_2$ or a pharmaceutically acceptable salt thereof selected from acetate salt or trifluoroacetate salt, and cyclosporine.

In some aspects, methods for treating an acute myocardial infarction injury in a mammalian subject are provided. In some embodiments, the methods include administering simultaneously, separately or sequentially an effective amount of (i) an aromatic-cationic peptide or a pharmaceutically acceptable salt thereof, and (ii) one or more additional active agents. In some embodiments, the aromatic-cationic peptide is selected from the group consisting of: Tyr-D-Arg-Phe-Lys-NH$_2$; 2',6'-Dmt-D-Arg-Phe-Lys-NH$_2$; Phe-D-Arg-Phe-Lys-NH$_2$; 2',6'-Dmp-D-Arg-Phe-Lys-NH$_2$; and D-Arg-2',6'-Dmt-Lys-Phe-NH$_2$. In some embodiments, the pharmaceutically acceptable salt comprises acetate salt or trifluoroacetate salt. In some embodiments, the additional active agent comprises cyclosporine or a cyclosporine derivative or analogue. In some embodiments of the method, the aromatic-cationic peptide comprises D-Arg-2',6'-Dmt-Lys-Phe-NH$_2$ or a pharmaceutically acceptable salt thereof selected from acetate salt or trifluoroacetate salt, and the additional active agent comprises cyclosporine.

In some embodiments of the method, the peptide and the one or more additional active agent(s) are administered in a manner selected from the group consisting of: simultaneously; sequentially in either order; sequentially in either order prior to performing a revascularization procedure on the subject; simultaneously prior to performing a revascularization procedure on the subject. In some embodiments of the method, the subject is administered the peptide and the one or more additional active agent(s) in a manner selected from the group consisting of: after a revascularization procedure; simultaneously or separately during and after performing a revascularization procedure on the subject. In some embodiments of the method, the subject is administered the peptide continuously before, during, and after a revascularization procedure and the subject is administered the additional one or more active agent(s) as a bolus dose immediately prior to the revascularization procedure. In some embodiments of the method, the subject is administered the one or more additional agent(s) before a revascularization procedure and the subject is administered the peptide continuously during and after the revascularization procedure. In some embodiments of the method, the subject is administered the one or more additional active agent(s) continuously before and during a revascularization procedure and the subject is administered the peptide continuously during and after the revascularization procedure.

In some embodiments of the method, the subject is administered the aromatic-cationic peptide for a time period selected from the group consisting of: at least 3 hours after a revascularization procedure; at least 5 hours after a revascularization procedure; at least 8 hours after a revascularization procedure; at least 12 hours after a revascularization procedure; at least 24 hours after a revascularization procedure. In some embodiments of the method, the subject is administered the aromatic-cationic peptide in a time period selected from the group consisting of: starting at least 8 hours before a revascularization procedure; starting at least 4 hours before a revascularization procedure; starting at least 2 hours before a revascularization procedure; starting at least 1 hour before a revascularization procedure; starting at least 30 minutes before a revascularization procedure. In some embodiments of the methods, the subject is administered the one or more additional active agent(s) in a time period selected from the group consisting of: starting at least 8 hours before a revascularization procedure; starting at least 4 hours before a revascularization procedure; starting at least 2 hours before a revascularization procedure; starting at least 1 hour before a revascularization procedure; starting at least 30 minutes before a revascularization procedure.

In some embodiments, the revascularization procedure is selected from the group consisting of: percutaneous coronary intervention; balloon angioplasty; insertion of a bypass graft; insertion of a stent; directional coronary atherectomy; treatment with a one or more thrombolytic agent(s); and removal of an occlusion.

In some aspects, kits for treating ischemia/reperfusion injury, e.g., acute myocardial infarction, in a mammalian subject are provided. In some embodiments, the kits include: (i) a peptide D-Arg-2,'6'-Dmt-Lys-Phe-NH$_2$ or a pharmaceutically acceptable salt thereof selected from acetate salt or trifluoroacetate salt, and (ii) cyclosporine, wherein the peptide and the cyclosporine are packaged in the same or separate vials.

In some aspects, methods for treating ischemia and/or reperfusion injury in a subject in need thereof are provided. In some embodiments, the methods include administering simultaneously, separately or sequentially an effective amount of (i) an aromatic-cationic peptide or a pharmaceutically acceptable salt thereof, and (ii) one or more additional active agent(s). In some embodiments, the aromatic-cationic peptide is selected from the group consisting of: Tyr-D-Arg-D-Arg-Phe-Lys-NH$_2$; 2',6'-Dmt-D-Arg-Phe-Lys-NH$_2$; Phe-D-Arg-Phe-Lys-NH$_2$; 2',6'-Dmp-D-Arg-Phe-Lys-NH$_2$; and D-Arg-2',6'-Dmt-Lys-Phe-NH$_2$. In some embodiments, the pharmaceutically acceptable salt comprises acetate salt or trifluoroacetate salt. In some embodiments, the one or more additional active agent(s) comprise cyclosporine or a cyclosporine derivative or analogue. In some embodiments, the aromatic-cationic peptide comprises D-Arg-2'6'-Dmt-Lys-Phe-NH$_2$ or a pharmaceutically acceptable salt thereof selected from acetate salt or trifluoroacetate salt, and the additional active agent comprises cyclosporine.

In some aspects, methods of preventing or reducing ischemia-reperfusion injury in a removed tissue organ of a mammal are provided. In some embodiments, the methods include: prior to organ removal, administering to the mammal simultaneously, separately or sequentially an effective amount of (i) an aromatic-cationic peptide or a pharmaceutically acceptable salt thereof, and (ii) one or more additional active agent(s). In some embodiments, the aromatic-cationic peptide is selected from the group consisting of: Tyr-D-Arg-Phe-Lys-NH$_2$; 2',6'-Dmt-D-Arg-Phe-Lys-NH$_2$; Phe-D-Arg-Phe-Lys-NH$_2$; 2',6'-Dmp-D-Arg-Phe-Lys-NH$_2$; and D-Arg-2',6'-Dmt-Lys-Phe-NH$_2$. In some embodiments, the pharmaceutically acceptable salt comprises acetate salt or trifluoroacetate salt. In some embodiments, the additional active agent comprises cyclosporine or a cyclosporine derivative or analogue. In some embodiments, the aromatic-cationic peptide comprises D-Arg-2',6'-Dmt-Lys-Phe-NH$_2$ or a pharmaceutically acceptable salt thereof selected from acetate salt or trifluoroacetate salt, and the additional active agent comprises cyclosporine.

In some embodiments, the method further comprising administering to the recipient of the removed organ an effective amount of (i) an aromatic-cationic peptide or a pharmaceutically acceptable salt thereof, and (ii) one or more additional active agent(s). In some embodiments, the aromatic-cationic peptide administered to the recipient is selected from the group consisting of: Tyr-D-Arg-Phe-Lys-NH$_2$; 2',6'-Dmt-D-Arg-Phe-Lys-NH$_2$; Phe-D-Arg-Phe-Lys-NH$_2$, 2',6'-Dmp-D-Arg-Phe-Lys-NH$_2$; and D-Arg-2',6'-Dmt-Lys-Phe-NH$_2$. In some embodiments, the pharmaceutically acceptable salt of the peptide administered to the recipient comprises acetate salt or trifluoroacetate salt. In some embodiments, the additional active agent administered to the recipient comprises cyclosporine or a cyclosporine derivative or analogue. In some embodiments, the aromatic-cationic peptide administered to the recipient comprises D-Arg-2',6'-Dmt-Lys-Phe-NH$_2$ or a pharmaceutically acceptable salt thereof selected from acetate salt or trifluoroacetate salt, and the additional active agent administered to the recipient comprises cyclosporine.

In other aspects, the present technology relates to the treatment or prevention of ischemia-reperfusion injury to a tissue or an organ before, during or after transplantation through administration, to the tissue or organ, of therapeutically effective amounts of aromatic-cationic peptides such as Tyr-D-Arg-Phe-Lys-NH$_2$; 2',6'-Dmt-D-Arg-Phe-Lys-NH$_2$; Phe-D-Arg-Phe-Lys-NH$_2$, 2',6'-Dmp-D-Arg-Phe-Lys-NH$_2$; and D-Argand D-Arg-2',6'-Dmt-Lys-Phe-NH$_2$ or pharmaceutically acceptable salts thereof (e.g., acetate salt or trifluoroacetate salt) and one or more active agents, such as cyclosporine or a cyclosporine derivative or analogue.

In some aspects, methods of coronary revascularization are provided. In some embodiments, the methods include: (a) administering to the mammal simultaneously, separately or sequentially an effective amount of (i) an aromatic-cationic peptide or a pharmaceutically acceptable salt thereof, and (ii) one or more additional active agent(s); (b) performing a coronary artery bypass graft procedure on the subject. In some embodiments, the aromatic-cationic peptide is selected from the group consisting of: Tyr-D-Arg-Phe-Lys-NH$_2$; 2',6'-Dmt-D-Arg-Phe-Lys-NH$_2$; Phe-D-Arg-Phe-Lys-NH$_2$; 2',6'-Dmp-D-Arg-Phe-Lys-NH$_2$; and D-Arg-2',6'-Dmt-Lys-Phe-NH$_2$. In some embodiments, the pharmaceutically acceptable salt comprises acetate salt or trifluoroacetate salt. In some embodiments, the additional active agent comprises cyclosporine or a cyclosporine derivative or analogue. In some embodiments, the aromatic-cationic peptide comprises D-Arg-2',6'-Dmt-Lys-Phe-NH$_2$ or a pharmaceutically acceptable salt thereof selected from acetate salt or trifluoroacetate salt, and the additional active agent comprises cyclosporine.

In some aspects, methods for the treatment, prevention or alleviation of symptoms of cyclosporine-induced nephrotoxicity in a subject in need thereof are provided. In some embodiments, the methods include (a) administering to the mammal simultaneously, separately or sequentially an effective amount of (i) an aromatic-cationic peptide or a pharmaceutically acceptable salt thereof, and (ii) one or more additional active agents. In some embodiments, the aromatic-cationic peptide is selected from the group consisting of: Tyr-D-Arg-Phe-Lys-NH$_2$; 2',6'-Dmt-D-Arg-Phe-Lys-NH$_2$; Phe-D-Arg-Phe-Lys-NH$_2$; 2',6'-Dmp-D-Arg-Phe-Lys-NH$_2$; and D-Arg-2',6'-Dmt-Lys-Phe-NH$_2$. In some embodiments, the pharmaceutically acceptable salt comprises acetate salt or trifluoroacetate salt. In some embodiments, the additional active agent comprises cyclosporine or a cyclosporine derivative or analogue. In some embodiments, the aromatic-cationic peptide comprises D-Arg-2',6'-Dmt-Lys-Phe-NH$_2$ or a pharmaceutically acceptable salt thereof selected from acetate salt or trifluoroacetate salt, and the additional active agent comprises cyclosporine.

In various embodiments, the peptide and active agent are administered simultaneously, separately, or sequentially to a subject in need thereof. In some embodiments, the peptide and the active agent are administered sequentially in either order. In some embodiments, the peptide and the additional active agent are administered sequentially in either order prior to performing a revascularization procedure on the subject. In some embodiments, the peptide and the additional active agent are administered simultaneously. In some embodiments, the peptide and the additional active agent are administered simultaneously prior to performing a revascularization procedure on the subject. In some embodiments, the additional active agent comprises cyclosporine or a cyclosporine derivative or analogue.

In another aspect, the present disclosure provides a kit for treating ischemia-reperfusion injury in a mammalian subject comprising: (i) a peptide D-Arg-2'6'-Dmt-Lys-Phe-NH$_2$ or a pharmaceutically acceptable salt and (ii) an additional active agent, wherein the peptide and active agent are packaged in the same or separate vials. In some embodiments, the additional active agent comprises cyclosporine or a cyclosporine derivative or analogue.

In some aspects, the present disclosure provides a method for treating an acute myocardial infarction injury in a mammalian subject, the method comprising administering simultaneously, separately or sequentially an effective amount of (i) a peptide D-Arg-2'6'-Dmt-Lys-Phe-NH$_2$ and (ii) an additional active agent. In some embodiments, the additional active agent comprises cyclosporine or a cyclosporine derivative or analogue.

In some embodiments, the additional active agent is a cardiovascular agent is selected from the group consisting of: hyaluronidase, a corticosteroid, recombinant superoxide dismutase, prostacyclin, fluosol, magnesium, poloxamer 188, trimetazidine, eniporidine, cariporidine, a nitrate, anti-P selectin, an anti-CD18 antibody, adenosine, and glucose-insulin-potassium. In some embodiments, the cardiovascular agent is selected from the group consisting of: an anti-arrhythymia agent, a vasodilator, an anti-anginal agent, a corticosteroid, a cardioglycoside, a diuretic, a sedative, an angiotensin converting enzyme (ACE) inhibitor, an angiotensin II antagonist, a thrombolytic agent, a calcium channel blocker, a throboxane receptor antagonist, a radical scavenger, an anti-platelet drug, a β-adrenaline receptor blocking drug, α-receptor blocking drug, a sympathetic nerve inhibitor, a digitalis formulation, an inotrope, and an antihyperlipidemic drug. In some embodiments, the cardiovascular agent is cyclosporine.

In some embodiments, the peptide and the additional active agent are administered sequentially in either order. In some embodiments, the peptide and the additional active agent are administered sequentially in either order prior to performing a revascularization procedure on the subject. In some embodiments, the peptide and the c additional active agent are administered simultaneously.

In some embodiments, the peptide and the additional active agent are administered simultaneously prior to performing a revascularization procedure on the subject. In some embodiments, the subject is administered the peptide and the additional active agent after a revascularization procedure. In some embodiments, the subject is administered the peptide and the additional active agent simultaneously or separately during and after performing a revascularization procedure on the subject. In some embodiments, the subject is administered the peptide continuously before, during, and after a revascularization procedure and the subject is administered the additional active agent as a bolus dose immediately prior to the revascularization procedure. In some embodiments, the subject is administered the additional active agent before a revascularization procedure and the subject is administered the peptide continuously during and after the revascularization procedure. In some embodiments, the subject is administered the additional active agent continuously before and during a revascularization procedure and the subject is administered the peptide continuously during and after the revascularization procedure. In some embodiments, the additional active agent comprises cyclosporine.

In some embodiments, the subject is administered the peptide for at least 3 hours after the revascularization procedure. In some embodiments, the subject is administered the peptide for at least 5 hours after the revascularization procedure. In some embodiments, the subject is administered the peptide for at least 8 hours after the revascularization procedure. In one some embodiments, the subject is administered the peptide for at least 12 hours after the revascularization procedure. In some embodiments, the subject is administered the peptide for at least 24 hours after the revascularization procedure.

In some embodiments, the subject is administered the peptide starting at least 8 hours before the revascularization procedure. In some embodiments, the subject is administered the peptide starting at least 4 hours before the revascularization procedure. In some embodiments, the subject is administered the peptide starting at least 2 hours before the revascularization procedure. In some embodiments, the subject is administered the peptide starting at least 1 hour before the revascularization procedure. In some embodiments, the subject is administered the peptide starting at least 30 minutes before the revascularization procedure.

In one embodiment, the revascularization procedure is selected from the group consisting of: percutaneous coronary intervention; balloon angioplasty; insertion of a bypass graft; insertion of a stent; or directional coronary atherectomy. In some embodiments, the revascularization procedure is removal of the occlusion. In some embodiments, the revascularization procedure includes administration of one or more thrombolytic agents. In some embodiments, the one or more thrombolytic agents are selected from the group consisting of: tissue plasminogen activator; urokinase; prourokinase; streptokinase; acylated form of plasminogen; acylated form of plasmin; and acylated streptokinase-plasminogen complex.

In another aspect, the present disclosure provides a method of coronary revascularization comprising: (a) administering simultaneously, separately or sequentially an effective amount of (i) a peptide D-Arg-2'6'-Dmt-Lys-Phe-NH$_2$ or a pharmaceutically acceptable salt and (ii) an additional active agent; and (b) performing a coronary artery bypass graft procedure on the subject. In some embodiments, the additional active agent comprises cyclosporine or a cyclosporine derivative or analogue.

In another aspect, the present disclosure provides a method of coronary revascularization comprising: (a) administering to a mammalian subject a therapeutically effective amount of the peptide D-Arg-2'6'-Dmt-Lys-Phe-NH$_2$ or a pharmaceutically acceptable salt thereof; (b) administering to the subject a therapeutically effective amount of cyclosporine or a cyclosporine derivative or analogue; and (c) performing a coronary artery bypass graft procedure on the subject.

In another aspect, the present disclosure provides a composition comprising: an (i) an aromatic-cationic peptide or a pharmaceutically acceptable salt thereof, and (ii) one or more additional active agents; wherein the aromatic-cationic peptide is linked to the active agent by a linker. In some embodiments, the aromatic-cationic peptide is selected from the group consisting of: Tyr-D-Arg-Phe-Lys-NH$_2$; 2',6'-Dmt-D-Arg-Phe-Lys-NH$_2$; Phe-D-Arg-Phe-Lys-NH$_2$; 2',6'-Dmp-D-Arg-Phe-Lys-NH$_2$; and D-Arg-2',6'-Dmt-Lys-Phe-NH$_2$. In some embodiments, the pharmaceutically acceptable salt comprises acetate salt or trifluoroacetate salt. In some embodiments, the additional active agent comprises cyclosporine or a cyclosporine derivative or analogue. In some embodiments, the aromatic-cationic peptide comprises D-Arg-2',6'-Dmt-Lys-Phe-NH$_2$ or a pharmaceutically acceptable salt thereof selected from acetate salt or trifluoroacetate salt, the additional active agent comprises cyclosporine, and the linker comprises an enzyme-cleavable linker.

In some embodiments, the aromatic-cationic peptide is a peptide having:
  at least one net positive charge;
  a minimum of four amino acids;
  a maximum of about twenty amino acids;
  a relationship between the minimum number of net positive charges ($p_m$) and the total number of amino acid residues (r) wherein $3p_m$ is the largest number that is less than or equal to r+1; and a relationship between the minimum number of aromatic groups (a) and the total number of net positive charges ($p_t$) wherein $2a$ is the largest number that is less than or equal to $p_t$+1, except that when a is 1, $p_t$ may also be 1. In particular embodiments, the mammalian subject is a human.

In some embodiments, $2p_m$ is the largest number that is less than or equal to r+1, and a may be equal to $p_t$. The aromatic-cationic peptide may be a water-soluble peptide having a minimum of two or a minimum of three positive charges.

In some embodiments, the peptide comprises one or more non-naturally occurring amino acids, for example, one or more D-amino acids. In some embodiments, the C-terminal carboxyl group of the amino acid at the C-terminus is amidated. In certain embodiments, the peptide has a minimum of four amino acids. The peptide may have a maximum of about 6, a maximum of about 9, or a maximum of about 12 amino acids.

In some embodiments, the peptide comprises a tyrosine or a 2',6'-dimethyltyrosine (Dmt) residue at the N-terminus. For example, the peptide may have the formula Tyr-D-Arg-Phe-Lys-NH$_2$ or 2',6'-Dmt-D-Arg-Phe-Lys-NH$_2$. In another embodiment, the peptide comprises a phenylalanine or a 2',6'-dimethylphenylalanine residue at the N-terminus. For example, the peptide may have the formula Phe-D-Arg-Phe-Lys-NH$_2$ or 2',6'-Dmp-D-Arg-Phe-Lys-NH$_2$. In a particular embodiment, the aromatic-cationic peptide has the formula D-Arg-2',6'-Dmt-Lys-Phe-NH$_2$.

In one embodiment, the peptide is defined by formula I:

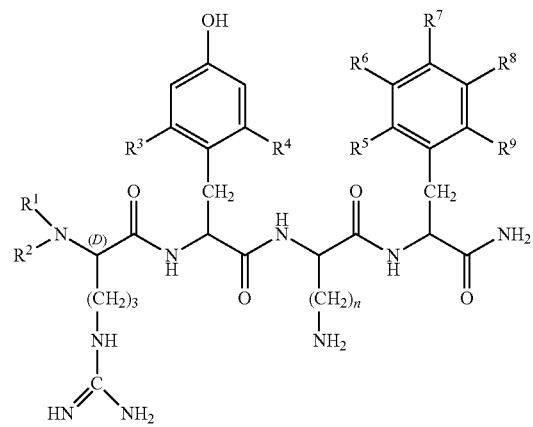

wherein $R^1$ and $R^2$ are each independently selected from
(i) hydrogen;
(ii) linear or branched $C_1$-$C_6$ alkyl;

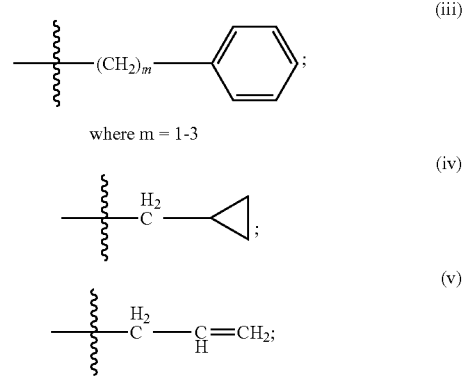

$R^3$ and $R^4$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo;

$R^5$, $R^6$, $R^7$, $R^8$, and $R^9$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo; and
n is an integer from 1 to 5.

In a particular embodiment, $R^1$ and $R^2$ are hydrogen; $R^3$ and $R^4$ are methyl; $R^5$, $R^6$, $R^7$, $R^8$, and $R^9$ are all hydrogen; and n is 4.

In some embodiments, the peptide is defined by formula II:

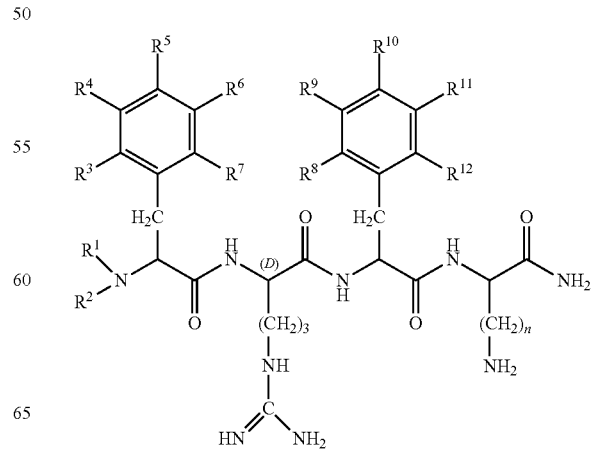

wherein $R_1$ and $R^2$ are each independently selected from
(i) hydrogen;
(ii) linear or branched $C_1$-$C_6$ alkyl;

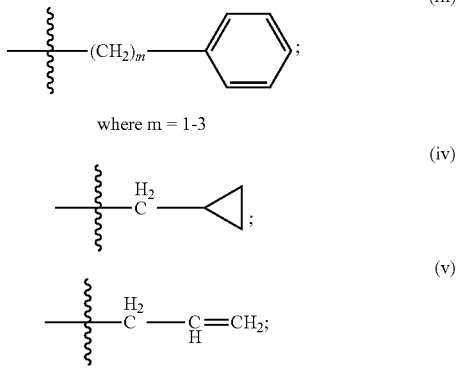

(iii) where m = 1-3

(iv)

(v)

$R_3$, $R_4$, $R_5$, $R_6$, $R_7$, $R_8$, $R_9$, $R_{10}$, $R_{11}$ and $R_{12}$ are each independently selected from
(i) hydrogen;
(ii) linear or branched $C_1$-$C_6$ alkyl;
(iii) $C_1$-$C_6$ alkoxy;
(iv) amino;
(v) $C_1$-$C_4$ alkylamino;
(vi) $C_1$-$C_4$ dialkylamino;
(vii) nitro;
(viii) hydroxyl;
(ix) halogen, where "halogen" encompasses chloro, fluoro, bromo, and iodo; and
n is an integer from 1 to 5.

In a particular embodiment, $R^1$, $R^2$, $R^3$, $R^4$, $R^5$, $R^6$, $R^7$, $R^8$, $R^9$, $R^{10}$, $R^{11}$ and $R^{12}$ are all hydrogen; and n is 4. In another embodiment, $R^1$, $R^2$, $R^3$, $R^4$, $R^5$, $R^6$, $R^7$, $R^9$, and $R^{11}$ are all hydrogen; $R^8$ and $R^{12}$ are methyl; $R^{10}$ is hydroxyl; and n is 4.

The aromatic-cationic peptides may be administered in a variety of ways. In some embodiments, the peptides may be administered orally, topically, intranasally, intraperitoneally, intravenously, subcutaneously, or transdermally (e.g., by iontophoresis).

DETAILED DESCRIPTION

It is to be appreciated that certain aspects, modes, embodiments, variations and features of the invention are described below in various levels of detail in order to provide a substantial understanding of the present invention.

In practicing the present invention, many conventional techniques in molecular biology, protein biochemistry, cell biology, immunology, microbiology and recombinant DNA are used. These techniques are well-known and are explained in, e.g., *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N.Y., 1989); *DNA Cloning: A Practical Approach*, Vols. I and II, Glover, Ed. (1985); *Oligonucleotide Synthesis*, Gait, Ed. (1984); *Nucleic Acid Hybridization*, Hames & Higgins, Eds. (1985); *Transcription and Translation*, Hames & Higgins, Eds. (1984); *Animal Cell Culture*, Freshney, Ed. (1986); *Immobilized Cells and Enzymes* (IRL Press, 1986); Perbal, *A Practical Guide to Molecular Cloning*; the series, *Meth. Enzymol.*, (Academic Press, Inc., 1984); *Gene Transfer Vectors for Mammalian Cells*, Miller & Calos, Eds. (Cold Spring Harbor Laboratory, NY, 1987); and *Meth. Enzymol.*, Vols. 154 and 155, Wu & Grossman, and Wu, Eds., respectively.

The definitions of certain terms as used in this specification are provided below. Unless defined otherwise, all technical and scientific terms used herein generally have the same meaning as commonly understood by one of ordinary skill in the art to which this invention belongs.

As used in this specification and the appended claims, the singular forms "a", "an" and "the" include plural referents unless the content clearly dictates otherwise. For example, reference to "a cell" includes a combination of two or more cells, and the like.

As used herein, the "administration" of an agent, drug, or peptide to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. Administration includes self-administration and the administration by another.

As used herein, the term "amino acid" includes naturally-occurring amino acids and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics refers to chemical compounds that have a structure that is different from the general chemical structure of an amino acid, but that functions in a manner similar to a naturally-occurring amino acid. Amino acids can be referred to herein by either their commonly known three letter symbols or by the one-letter symbols recommended by the IUPAC-IUB Biochemical Nomenclature Commission.

As used herein, the term "active agent" and "therapeutic agent" are used interchangeably and refer to compounds useful for treating or preventing a disease or condition. For example, in some embodiments, active agents include aromatic-cationic peptides, cardiovascular agents, immunosuppressive agents, diuretics, sedatives, etc. In some embodiments, an active agent is administered alone or in combination with a one or more additional active agents. For example, in some embodiments, an aromatic-cationic peptide, or a pharmaceutically acceptable salt thereof, such as acetate salt or trifluoroacetate salt, and cyclosporine are provided.

As used herein, the terms "cardiovascular agent" or "cardiovascular drug" refers to a therapeutic compound that is useful for treating or preventing a cardiovascular disease or condition. Non-limiting examples of suitable cardiovascular agents include ACE inhibitors (angiotensin II converting enzyme inhibitors), ARB's (angiotensin II receptor antagonists), adrenergic blockers, adrenergic agonists, anti-anginal agents, anti-arrhythmics, anti-platelet agents, anti-coagulants, anti-hypertensives, anti-lipemic agents, calcium channel blockers, COX-2 inhibitors, diuretics, endothelin receptor antagonists, HMG Co-A reductase inhibitors, inotropic agents, rennin inhibitors, vasodialators, vasopressors, AGE crosslink breakers, and AGE formation inhibitors (advanced glycosylation end-product formation inhibitors, such as pimagedine), and combinations thereof. In some embodiments, the cardiovascular agent comprises cyclosporine.

In some embodiments, an active agent is an immunosuppressive agent. As used herein an "immunosuppressive agent" refers to a medication that slows or halts immune system activity. Immunosuppressive agents may be given to prevent the body from mounting an immune response after an organ transplant or for treating a disease that is caused by an overactive immune system. In some embodiments, immunosuppressive agents include glucocorticoids, cytostatics, antibodies, drugs acting on immunophilins and other drugs. Cyclosporine is an immunosuppressant drug used extensively to prevent organ rejection following allogenic transplants. It remains an important tool for managing organ transplantation despite having deleterious effects on renal structure and function. Nephrotoxicity is a primary limiting side-effect of cyclosporine, and is thought to result from low-grade hypoxic injury to renal tubular cells. A progressive loss of renal cells leads to interstitial fibrosis and a loss of renal function. It is known that apoptotic cell death occurs in cyclosporine-associated fibrosis with little evidence of necrotic cell death. Moreover, it has been shown that the expression of the apoptosis regulatory genes p53, Bax, Fas-L, Bcl-2, interleukin-converting enzyme (ICE), and caspase-3 favor cell death in cyclosporine-exposed renal cells. Cyclosporine has also been shown to be effective in the treatment psoriasis, atopic dermatitis, pyoderma gangrenosum, chronic autoimmune urticaria, and, rheumatoid arthritis. However, because of the high degree of toxicity associated with the drug, cyclosporine is typically indicated for severe cases of these conditions. For transplant patients, cyclosporine is generally administered only intermittently, or cyclically, with close monitoring of renal function.

As used herein, the term "cyclosporine" refers to cyclosporine A, cyclosporine G, and functional derivatives or analogues thereof, e.g., NIM811. Cyclosporine A refers to the natural *Tolypocladium inflatum* cyclic non-ribosomal peptide. Cyclosporine G differs from cyclosporine A in the amino acid 2 position, where an L-norvaline replaces the α-aminobutyric acid. (See generally, Wenger, R. M. 1986. Synthesis of Ciclosporin and analogues: structural and conformational requirements for immunosuppressive activity. Progress in Allergy, 38:46-64). In some embodiments disclosed herein, the combination of an aromatic-cationic peptide such as D-Arg-2',6'-Dmt-Lys-Phe-NH$_2$ and cyclosporine are provided.

As used herein, the term "effective amount" refers to a quantity sufficient to achieve a desired therapeutic and/or prophylactic effect, e.g., an amount which results in the prevention of, or a decrease in, ischemia-reperfusion injury or one or more symptoms associated with ischemia-reperfusion injury. In the context of therapeutic or prophylactic applications, the amount of a composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions can also be administered in combination with one or more additional therapeutic agents.

In the methods described herein, the aromatic-cationic peptides and one or more additional therapeutic agents may be administered to a subject having one or more signs or symptoms of acute myocardial infarction injury. In other embodiments, the mammal has one or more signs or symptoms of myocardial infarction, such as chest pain described as a pressure sensation, fullness, or squeezing in the mid portion of the thorax; radiation of chest pain into the jaw or teeth, shoulder, arm, and/or back; dyspnea or shortness of breath; epigastric discomfort with or without nausea and vomiting; and diaphoresis or sweating. For example, a "therapeutically effective amount" of the aromatic-cationic peptides and/or an additional active agent, such as a cardiovascular agent is meant levels in which the physiological effects of an acute myocardial infarction injury are, at a minimum, ameliorated. In some embodiments, the additional active agent is a cardiovascular agents such as cyclosporine, or functional derivatives or analogues thereof.

In some embodiments described herein, an aromatic-cationic peptide and one or more additional therapeutic agents are administered to a donor subject and/or a recipient subject prior to, during and/or after organ or tissue transplant. For example, in some embodiments, an aromatic-cationic peptide and one or more additional therapeutic agents ("combination therapy") may be administered to a first subject from which a tissue or organ will be removed for transplantation into a second subject. Additionally or alternatively, in some embodiments, the combination therapy is administered the extracted tissue or organ, prior to introduction into the second subject. Additionally or alternatively, in some embodiments, the combination therapy is administered to the second subject before, during and/or after organ or tissue transplant.

In some embodiments, the combination therapy (e.g., an aromatic-cationic peptide and one or more active agents, such as a cardiovascular agent, an immunosuppressive agent, etc.) is administered to a transplant recipient presenting with one or more signs or symptoms of ischemia-reperfusion injury due to, for example, organ or tissue transplant reperfusion problems (e.g., occlusions, necrotic tissue) and/or tissue or organ rejection. The signs and symptoms may vary depending on the type and location of the transplanted organ or tissue. For example, patients who reject a kidney may have less urine, and patients who reject a heart may have symptoms of heart failure. Additional signs or symptoms of organ or tissue rejection include, but are not limited to: the organ or tissue does not function properly, general discomfort, uneasiness, or ill feeling, pain or swelling in the location of the organ or tissue and fever. Thus, in some embodiments, a "therapeutically effective amount" of the aromatic-cationic peptides and/or second active agent means a levels in which the physiological effects of ischemia-reperfusion injury in an organ or tissue transplant are, at a minimum, ameliorated. In some embodiments, the second active agent comprises cyclosporine or functional derivatives or analogues thereof.

As used herein the term "ischemia reperfusion injury" refers to the damage caused by the restriction of blood supply to a tissue followed by a sudden resupply of blood and the attendant generation of free radicals. Such injury can occur, for example, after myocardial infarction or as a result of organ or tissue transplantation.

An "isolated" or "purified" polypeptide or peptide is substantially free of cellular material or other contaminating polypeptides from the cell or tissue source from which the agent is derived, or substantially free from chemical precursors or other chemicals when chemically synthesized. For example, an isolated aromatic-cationic peptide would be free of materials that would interfere with diagnostic or therapeutic uses of the agent. Such interfering materials may include enzymes, hormones and other proteinaceous and nonproteinaceous solutes.

As used herein, the terms "polypeptide", "peptide", and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art.

As used herein, the term "simultaneous" therapeutic use refers to the administration of at least two active ingredients by the same route and at the same time or at substantially the same time.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, the terms "treating" or "treatment" or "alleviation" refers to both therapeutic treatment and prophylactic or preventative measures, wherein the object is to prevent or slow down (lessen) the targeted pathologic condition or disorder. A subject is successfully "treated" for ischemia reperfusion injury if, after receiving a therapeutic amount of the aromatic-cationic peptides and one or more additional active agents according to the methods described herein, the subject shows observable and/or measurable reduction in or absence of one or more signs and symptoms of ischemia reperfusion injury, such as, e.g., reduced infarct size. It is also to be appreciated that the various modes of treatment or prevention of medical conditions as described are intended to mean "substantial", which includes total but also less than total treatment or prevention, and wherein some biologically or medically relevant result is achieved.

As used herein, "prevention" or "preventing" of a disorder or condition refers to one or more compounds that, in a statistical sample, reduces the occurrence of the disorder or condition in the treated sample relative to an untreated control sample, or delays the onset or reduces the severity of one or more symptoms of the disorder or condition relative to the untreated control sample. As used herein, preventing ischemia-reperfusion injury includes preventing oxidative damage or preventing mitochondrial permeability transitioning, thereby preventing or ameliorating the harmful effects of the loss and subsequent restoration of blood flow to the heart or other organs or tissues.

Methods of Prevention or Treatment

The present technology relates to compositions and methods for the treatment and prevention of diseases and/or conditions. Typically, the compositions and methods include an aromatic-cationic peptide or a pharmaceutically acceptable salt thereof, such as acetate salt or trifluoroacetate salt, and one or more active agents. In some embodiments, the aromatic-cationic peptide comprises one or more of Tyr-D-Arg-Phe-Lys-NH$_2$; 2',6'-Dmt-D-Arg-Phe-Lys-NH$_2$, Phe-D-Arg-Phe-Lys-NH$_2$; 2',6'-Dmp-D-Arg-Phe-Lys-NH$_2$; and D-Arg-2',6'-Dmt-Lys-Phe-NH$_2$, or a pharmaceutically acceptable salt thereof, such as acetate salt or trifluoroacetate salt, and the one or more active agents comprises cyclosporine or a functional derivative or analogue thereof, such as NIM811. In some embodiments, the aromatic-cationic peptide comprises D-Arg-2',6'-Dmt-Lys-Phe-NH$_2$, or a pharmaceutically acceptable salt thereof, such as acetate salt or trifluoroacetate salt, and the additional active agent comprises cyclosporine. In some embodiments the aromatic-cationic peptide comprises D-Arg-2',6'-Dmt-Lys-Phe-NH$_2$, or a pharmaceutically acceptable salt thereof, such as acetate salt or trifluoroacetate salt, and the additional active agent comprises or a functional derivative or analogue of cyclosporine, such as NIM811. The present technology relates to the treatment or prevention of ischemia-reperfusion injury by administration of certain aromatic-cationic peptides and one or more additional active agents to a subject in need thereof. The present technology also relates to the treatment or prevention of acute myocardial infarction injury or transplantation injury by administration of aromatic-cationic peptides, or a pharmaceutically acceptable salt thereof, such as acetate salt or trifluoroacetate salt, and one or more additional therapeutic agents to a subject in need thereof. In some embodiments, the therapeutic agents are administered in conjunction with a revascularization procedure. Also provided is a method for the treatment or prevention of ischemia-reperfusion injury in the heart or other organs or tissues. Also provided is a method of treating a myocardial infarction in a subject to prevent injury to the heart upon reperfusion. In one aspect, the present technology relates to a method of coronary revascularization comprising administering to a mammalian subject a therapeutically effective amount of the aromatic cationic peptide and performing coronary artery bypass graft (CABG) procedure on the subject. In some embodiments, the additional active agent comprises cyclosporine.

In one embodiment, the aromatic-cationic peptides and/or one or more agents are administered in dosages that are sub-therapeutic for each agent when administered separately. However, the combination of the two agents results in synergism, which provides an enhanced effect that is not observed when each of the agents are administered individually at higher doses. In one embodiment, the administration of the aromatic-cationic peptide and one or more agents "primes" the tissue, so that it is more responsive to the therapeutic effects of the other agent. For this reason, a lower dose of the aromatic-cationic peptide and one or more agents can be administered, and yet, a therapeutic effect is still observed.

In one embodiment, the subject is administered the peptide and one or more additional active agents simultaneously, separately, or sequentially prior to a revascularization procedure (e.g., in transplant or after myocardial infarction). In another embodiment, the subject is administered the peptide and one or more additional active agents simultaneously, separately, or sequentially after the revascularization procedure. In another embodiment, the subject is administered the peptide and one or more additional active agents simultaneously, separately, or sequentially during and after the revascularization procedure. In yet another embodiment, the subject is administered the peptide and one or more additional active agents simultaneously or separately continuously before, during, and after the revascularization procedure. In another embodiment, the subject is administered the peptide and one or more additional active agents regularly (i.e., chronically) following a transplant, an AMI and/or a revascularization or CABG procedure. In some embodiments, the additional active agent comprises cyclosporine.

In one embodiment, the subject is administered the peptide and/or one or more additional active agents for at least 3 hours, at least 5 hours, at least 8 hours, at least 12 hours, or at least 24 hours after the revascularization procedure. In one embodiment, the subject is administered the peptide and/or one or more additional active agents starting at least 8 hours, at least 4 hours, at least 2 hours, at least 1 hour, or at least 30 minutes prior to the revascularization procedure. In one embodiment, the subject is administered the peptide and/or one or more additional active agents for at least one week, at least one month or at least one year after the revascularization procedure. In some embodiments, the additional active agent comprises cyclosporine.

Aromatic-cationic peptides are water-soluble and highly polar. Despite these properties, the peptides can readily penetrate cell membranes. The aromatic-cationic peptides typically include a minimum of three amino acids or a minimum of four amino acids, covalently joined by peptide bonds. The maximum number of amino acids present in the aromatic-cationic peptides is about twenty amino acids covalently joined by peptide bonds. Suitably, the maximum number of amino acids is about twelve, more preferably about nine, and most preferably about six.

The amino acids of the aromatic-cationic peptides can be any amino acid. As used herein, the term "amino acid" is used to refer to any organic molecule that contains at least one amino group and at least one carboxyl group. Typically, at least one amino group is at the α position relative to a carboxyl group. The amino acids may be naturally occurring. Naturally occurring amino acids include, for example, the twenty most common levorotatory (L) amino acids normally found in mammalian proteins, i.e., alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr), and valine (Val). Other naturally occurring amino acids include, for example, amino acids that are synthesized in metabolic processes not associated with protein synthesis. For example, the amino acids ornithine and citrulline are synthesized in mammalian metabolism during the production of urea. Another example of a naturally occurring amino acid includes hydroxyproline (Hyp).

The peptides optionally contain one or more non-naturally occurring amino acids. For example, the peptide may have no amino acids that are naturally occurring. The non-naturally occurring amino acids may be levorotary (L-), dextrorotatory (D-), or mixtures thereof. Non-naturally occurring amino acids are those amino acids that typically are not synthesized in normal metabolic processes in living organisms, and do not naturally occur in proteins. In addition, the non-naturally occurring amino acids suitably are also not recognized by common proteases. The non-naturally occurring amino acid can be present at any position in the peptide. For example, the non-naturally occurring amino acid can be at the N-terminus, the C-terminus, or at any position between the N-terminus and the C-terminus.

The non-natural amino acids may, for example, comprise alkyl, aryl, or alkylaryl groups not found in natural amino acids. Some examples of non-natural alkyl amino acids include α-aminobutyric acid, β-aminobutyric acid, γ-aminobutyric acid, δ-aminovaleric acid, and ε-aminocaproic acid. Some examples of non-natural aryl amino acids include ortho-, meta, and para-aminobenzoic acid. Some examples of non-natural alkylaryl amino acids include ortho-, meta-, and para-aminophenylacetic acid, and γ-phenyl-β-aminobutyric acid. Non-naturally occurring amino acids include derivatives of naturally occurring amino acids. The derivatives of naturally occurring amino acids may, for example, include the addition of one or more chemical groups to the naturally occurring amino acid.

For example, one or more chemical groups can be added to one or more of the 2', 3', 4', 5', or 6' position of the aromatic ring of a phenylalanine or tyrosine residue, or the 4', 5', 6', or 7' position of the benzo ring of a tryptophan residue. The group can be any chemical group that can be added to an aromatic ring. Some examples of such groups include branched or unbranched $C_1$-$C_4$ alkyl, such as methyl, ethyl, n-propyl, isopropyl, butyl, isobutyl, or t-butyl, $C_1$-$C_4$ alkyloxy (i.e., alkoxy), amino, $C_1$-$C_4$ alkylamino and $C_1$-$C_4$ dialkylamino (e.g., methylamino, dimethylamino), nitro, hydroxyl, halo (i.e., fluoro, chloro, bromo, or iodo). Some specific examples of non-naturally occurring derivatives of naturally occurring amino acids include norvaline (Nva) and norleucine (Nle).

Another example of a modification of an amino acid in a peptide is the derivatization of a carboxyl group of an aspartic acid or a glutamic acid residue of the peptide. One example of derivatization is amidation with ammonia or with a primary or secondary amine, e.g. methylamine, ethylamine, dimethylamine or diethylamine. Another example of derivatization includes esterification with, for example, methyl or ethyl alcohol. Another such modification includes derivatization of an amino group of a lysine, arginine, or histidine residue. For example, such amino groups can be acylated. Some suitable acyl groups include, for example, a benzoyl group or an alkanoyl group comprising any of the $C_1$-$C_4$ alkyl groups mentioned above, such as an acetyl or propionyl group.

The non-naturally occurring amino acids are preferably resistant, and more preferably insensitive, to common proteases. Examples of non-naturally occurring amino acids that are resistant or insensitive to proteases include the dextrorotatory (D-) form of any of the above-mentioned naturally occurring L-amino acids, as well as L- and/or D-non-naturally occurring amino acids. The D-amino acids do not normally occur in proteins, although they are found in certain peptide antibiotics that are synthesized by means other than the normal ribosomal protein synthetic machinery of the cell. As used herein, the D-amino acids are considered to be non-naturally occurring amino acids.

In order to minimize protease sensitivity, the peptides should have less than five, preferably less than four, more preferably less than three, and most preferably, less than two contiguous L-amino acids recognized by common proteases, irrespective of whether the amino acids are naturally or non-naturally occurring. Optimally, the peptide has only D-amino acids, and no L-amino acids. If the peptide contains protease sensitive sequences of amino acids, at least one of the amino acids is preferably a non-naturally-occurring D-amino acid, thereby conferring protease resistance. An example of a protease sensitive sequence includes two or more contiguous basic amino acids that are readily cleaved by common proteases, such as endopeptidases and trypsin. Examples of basic amino acids include arginine, lysine and histidine.

The aromatic-cationic peptides should have a minimum number of net positive charges at physiological pH in comparison to the total number of amino acid residues in the peptide. The minimum number of net positive charges at physiological pH will be referred to below as ($p_m$). The total number of amino acid residues in the peptide will be referred to below as (r). The minimum number of net positive charges discussed below are all at physiological pH. The term "physiological pH" as used herein refers to the normal pH in the cells of the tissues and organs of the mammalian body. For instance, the physiological pH of a human is normally approximately 7.4, but normal physiological pH in mammals may be any pH from about 7.0 to about 7.8.

"Net charge" as used herein refers to the balance of the number of positive charges and the number of negative charges carried by the amino acids present in the peptide. In this specification, it is understood that net charges are measured at physiological pH. The naturally occurring amino acids that are positively charged at physiological pH include L-lysine, L-arginine, and L-histidine. The naturally occurring amino acids that are negatively charged at physiological pH include L-aspartic acid and L-glutamic acid. Typically, a peptide has a positively charged N-terminal amino group and a negatively charged C-terminal carboxyl group. The charges cancel each other out at physiological pH.

In one embodiment, the aromatic-cationic peptides have a relationship between the minimum number of net positive charges at physiological pH ($p_m$) and the total number of amino acid residues (r) wherein $3p_m$ is the largest number that is less than or equal to r+1. In this embodiment, the relationship between the minimum number of net positive charges ($p_m$) and the total number of amino acid residues (r) is as follows:

TABLE 1

Amino acid number and net positive charges ($3p_m \leq p + 1$)

| (r) | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|
| ($p_m$) | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of net positive charges ($p_m$) and the total number of amino acid residues (r) wherein $2p_m$ is the largest number that is less than or equal to r+1. In this embodiment, the relationship between the minimum number of net positive charges ($p_m$) and the total number of amino acid residues (r) is as follows:

TABLE 2

Amino acid number and net positive charges ($2p_m \leq p + 1$)

| (r) | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|
| ($p_m$) | 2 | 2 | 3 | 3 | 4 | 4 | 5 | 5 | 6 | 6 | 7 | 7 | 8 | 8 | 9 | 9 | 10 | 10 |

In one embodiment, the minimum number of net positive charges ($p_m$) and the total number of amino acid residues (r) are equal. In another embodiment, the peptides have three or four amino acid residues and a minimum of one net positive charge, suitably, a minimum of two net positive charges and more preferably a minimum of three net positive charges.

It is also important that the aromatic-cationic peptides have a minimum number of aromatic groups in comparison to the total number of net positive charges ($p_t$). The minimum number of aromatic groups will be referred to below as (a). Naturally occurring amino acids that have an aromatic group include the amino acids histidine, tryptophan, tyrosine, and phenylalanine. For example, the hexapeptide Lys-Gln-Tyr-D-Arg-Phe-Trp has a net positive charge of two (contributed by the lysine and arginine residues) and three aromatic groups (contributed by tyrosine, phenylalanine and tryptophan residues).

The aromatic-cationic peptides should also have a relationship between the minimum number of aromatic groups (a) and the total number of net positive charges at physiological pH ($p_t$) wherein 3a is the largest number that is less than or equal to $p_t+1$, except that when $p_t$ is 1, a may also be 1. In this embodiment, the relationship between the minimum number of aromatic groups (a) and the total number of net positive charges ($p_t$) is as follows:

TABLE 3

Aromatic groups and net positive charges ($3a \leq p_t + 1$ or $a = p_t = 1$)

| ($p_t$) | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| (a) | 1 | 1 | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of aromatic groups (a) and the total number of net positive charges ($p_t$) wherein 2a is the largest number that is less than or equal to $p_t+1$. In this embodiment, the relationship between the minimum number of aromatic amino acid residues (a) and the total number of net positive charges ($p_t$) is as follows:

TABLE 4

Aromatic groups and net positive charges ($2a \leq p_t + 1$ or $a = p_t = 1$)

| ($p_t$) | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| (a) | 1 | 1 | 2 | 2 | 3 | 3 | 4 | 4 | 5 | 5 | 6 | 6 | 7 | 7 | 8 | 8 | 9 | 9 | 10 | 10 |

In another embodiment, the number of aromatic groups (a) and the total number of net positive charges ($p_t$) are equal. In one embodiment, the aromatic-cationic peptide is a tripeptide having two net positive charges and at least one aromatic amino acid. In a particular embodiment, the aromatic-cationic peptide is a tripeptide having two net positive charges and two aromatic amino acids.

Carboxyl groups, especially the terminal carboxyl group of a C-terminal amino acid, are suitably amidated with, for example, ammonia to form the C-terminal amide. Alternatively, the terminal carboxyl group of the C-terminal amino acid may be amidated with any primary or secondary amine. The primary or secondary amine may, for example, be an alkyl, especially a branched or unbranched $C_1$-$C_4$ alkyl, or an aryl amine. Accordingly, the amino acid at the C-terminus of the peptide may be converted to an amido, N-methylamido, N-ethylamido, N,N-dimethylamido, N,N-diethylamido, N-methyl-N-ethylamido, N-phenylamido or N-phenyl-N-ethylamido group. The free carboxylate groups of the asparagine, glutamine, aspartic acid, and glutamic acid residues not occurring at the C-terminus of the aromatic-cationic peptides may also be amidated wherever they occur within the peptide. The amidation at these internal positions may be with ammonia or any of the primary or secondary amines described above.

Aromatic-cationic peptides include, but are not limited to, the following peptide examples:

Lys-D-Arg-Tyr-NH₂

Phe-D-Arg-His

D-Tyr-Trp-Lys-NH₂

Trp-D-Lys-Tyr-Arg-NH₂

Tyr-His-D-Gly-Met

Phe-Arg-D-His-Asp

Tyr-D-Arg-Phe-Lys-Glu-NH₂

Met-Tyr-D-Lys-Phe-Arg

D-His-Glu-Lys-Tyr-D-Phe-Arg

Lys-D-Gln-Tyr-Arg-D-Phe-Trp-NH₂

Phe-D-Arg-Lys-Trp-Tyr-D-Arg-His

Gly-D-Phe-Lys-Tyr-His-D-Arg-Tyr-NH₂

Val-D-Lys-His-Tyr-D-Phe-Ser-Tyr-Arg-NH₂

Trp-Lys-Phe-D-Asp-Arg-Tyr-D-His-Lys

Lys-Trp-D-Tyr-Arg-Asn-Phe-Tyr-D-His-NH₂

Thr-Gly-Tyr-Arg-D-His-Phe-Trp-D-His-Lys

Asp-D-Trp-Lys-Tyr-D-His-Phe-Arg-D-Gly-Lys-NH₂

D-His-Lys-Tyr-D-Phe-Glu-D-Asp-D-His-D-Lys-Arg-Trp-NH₂

Ala-D-Phe-D-Arg-Tyr-Lys-D-Trp-His-D-Tyr-Gly-Phe

Tyr-D-His-Phe-D-Arg-Asp-Lys-D-Arg-His-Trp-D-His-

-continued

Phe

Phe-Phe-D-Tyr-Arg-Glu-Asp-D-Lys-Arg-D-Arg-His-
Phe-NH$_2$

Phe-Try-Lys-D-Arg-Trp-His-D-Lys-D-Lys-Glu-Arg-D-
Tyr-Thr

Tyr-Asp-D-Lys-Tyr-Phe-D-Lys-D-Arg-Phe-Pro-D-Tyr-
His-Lys

Glu-Arg-D-Lys-Tyr-D-Val-Phe-D-His-Trp-Arg-D-Gly-
Tyr-Arg-D-Met-NH$_2$

Arg-D-Leu-D-Tyr-Phe-Lys-Glu-D-Lys-Arg-D-Trp-Lys-D-
Phe-Tyr-D-Arg-Gly

D-Glu-Asp-Lys-D-Arg-D-His-Phe-Phe-D-Val-Tyr-Arg-
Tyr-D-Tyr-Arg-His-Phe-NH$_2$

Asp-Arg-D-Phe-Cys-Phe-D-Arg-D-Lys-Tyr-Arg-D-Tyr-
Trp-D-His-Tyr-D-Phe-Lys-Phe

His-Tyr-D-Arg-Trp-Lys-Phe-D-Asp-Ala-Arg-Cys-D-Tyr-
His-Phe-D-Lys-Tyr-His-Ser-NH$_2$

Gly-Ala-Lys-Phe-D-Lys-Glu-Arg-Tyr-His-D-Arg-D-Arg-
Asp-Tyr-Trp-D-His-Trp-His-D-Lys-Asp

Thr-Tyr-Arg-D-Lys-Trp-Tyr-Glu-Asp-D-Lys-D-Arg-His-
Phe-D-Tyr-Gly-Val-Ile-D-His-Arg-Tyr-Lys-NH$_2$

In one embodiment, the aromatic-cationic peptide has the formula Phe-D-Arg-Phe-Lys-NH$_2$ (also referred to herein as "SS-20"). In another embodiment, the aromatic-cationic peptide has the formula D-Arg-2'6'1-Dmt-Lys-Phe-NH$_2$ (also referred to herein as "SS-31"). In some embodiments, the aromatic-cationic peptides have mu-opioid receptor agonist activity (i.e., they activate the mu-opioid receptor). Mu-opioid activity can be assessed by radioligand binding to cloned mu-opioid receptors or by bioassays using the guinea pig ileum (Schiller et al., *Eur J Med Chem*, 35:895-901, 2000; Zhao et al., *J Pharmacol Exp Ther*, 307:947-954, 2003). Peptides which have mu-opioid receptor agonist activity are typically those peptides which have a tyrosine residue or a tyrosine derivative at the N-terminus (i.e., the first amino acid position). Suitable derivatives of tyrosine include 2'-methyltyrosine methyltyrosine (Mmt); 2',6'-dimethyltyrosine (2'6'-Dmt); 3',5'-dimethyltyrosine (3'5'Dmt); N,2',6'-trimethyltyrosine (Tmt); and 2'-hydroxy-6'-methyl-tryosine (Hmt).

In one embodiment, a peptide that has mu-opioid receptor agonist activity has the formula Tyr-D-Arg-Phe-Lys-NH$_2$ (also referred to as "SS-01"). This peptide has a net positive charge of three, contributed by the amino acids tyrosine, arginine, and lysine and has two aromatic groups contributed by the amino acids phenylalanine and tyrosine. The tyrosine can be a modified derivative of tyrosine such as in 2',6'-dimethyltyrosine (2', 6'-Dmt) to produce the compound having the formula 2',6'-Dmt-D-Arg-Phe-Lys-NH$_2$ (also referred to as "SS-02"). This peptide has a molecular weight of 640 and carries a net three positive charge at physiological pH. The peptide readily penetrates the plasma membrane of several mammalian cell types in an energy-independent manner (Zhao et al., *J. Pharmacol Exp Ther.*, 304:425-432, 2003).

Peptides that do not have mu-opioid receptor agonist activity generally do not have a tyrosine residue or a derivative of tyrosine at the N-terminus (i.e., amino acid position 1). The amino acid at the N-terminus can be any naturally occurring or non-naturally occurring amino acid other than tyrosine. In one embodiment, the amino acid at the N-terminus is phenylalanine or its derivative. Exemplary derivatives of phenylalanine include 2'-methylphenylalanine (Mmp), 2',6'-dimethylphenylalanine (2',6'-Dmp), N,2',6'-trimethylphenylalanine (Tmp), and 2'-hydroxy-6'-methyl-phenylalanine (Hmp).

An example of an aromatic-cationic peptide that does not have mu-opioid receptor agonist activity has the formula Phe-D-Arg-Phe-Lys-NH$_2$ (also referred to as "SS-20"). Alternatively, the N-terminal phenylalanine can be a derivative of phenylalanine such as 2',6'-dimethylphenylalanine (2'6'-Dmp). In one embodiment, a peptide with 2',6'-dimethylphenylalanine at amino acid position 1 has the formula 2',6'-Dmp-D-Arg-Phe-Lys-NH$_2$. In one embodiment, the amino acid sequence is rearranged such that Dmt is not at the N-terminus. An example of such an aromatic-cationic peptide that does not have mu-opioid receptor agonist activity has the formula D-Arg-2'6'-Dmt-Lys-Phe-NH$_2$ (also referred to as "SS-31").

The peptides mentioned herein and their derivatives can further include functional analogues. A peptide is considered a functional analogue if the analogue has the same function as the stated peptide. The analogue may, for example, be a substitution variant of a peptide, wherein one or more amino acids are substituted by another amino acid. Suitable substitution variants of the peptides include conservative amino acid substitutions. Amino acids may be grouped according to their physicochemical characteristics as follows:

(a) Non-polar amino acids: Ala(A) Ser(S) Thr(T) Pro(P) Gly(G) Cys (C);
(b) Acidic amino acids: Asn(N) Asp(D) Glu(E) Gln(Q);
(c) Basic amino acids: His(H) Arg(R) Lys(K);
(d) Hydrophobic amino acids: Met(M) Leu(L) Ile(I) Val (V); and
(e) Aromatic amino acids: Phe(F) Tyr(Y) Trp(W) His (H).

Substitutions of an amino acid in a peptide by another amino acid in the same group is referred to as a conservative substitution and may preserve the physicochemical characteristics of the original peptide. In contrast, substitutions of an amino acid in a peptide by another amino acid in a different group is generally more likely to alter the characteristics of the original peptide.

Examples of peptides that activate mu-opioid receptors include, but are not limited to, the aromatic-cationic peptides shown in Table 5.

TABLE 5

Peptide Analogues with Mu-Opioid Activity

| Amino Acid Position 1 | Amino Acid Position 2 | Amino Acid Position 3 | Amino Acid Position 4 | C-Terminal Modification |
|---|---|---|---|---|
| Tyr | D-Arg | Phe | Lys | NH$_2$ |
| Tyr | D-Arg | Phe | Orn | NH$_2$ |
| Tyr | D-Arg | Phe | Dab | NH$_2$ |
| Tyr | D-Arg | Phe | Dap | NH$_2$ |
| 2'6'Dmt | D-Arg | Phe | Lys | NH$_2$ |

TABLE 5-continued

Peptide Analogues with Mu-Opioid Activity

| Amino Acid Position 1 | Amino Acid Position 2 | Amino Acid Position 3 | Amino Acid Position 4 | C-Terminal Modification |
|---|---|---|---|---|
| 2'6'Dmt | D-Arg | Phe | Lys-NH(CH$_2$)$_2$-NH-dns | NH$_2$ |
| 2'6'Dmt | D-Arg | Phe | Lys-NH(CH$_2$)$_2$-NH-atn | NH$_2$ |
| 2'6'Dmt | D-Arg | Phe | dnsLys | NH$_2$ |
| 2'6'Dmt | D-Cit | Phe | Lys | NH$_2$ |
| 2'6'Dmt | D-Cit | Phe | Ahp | NH$_2$ |
| 2'6'Dmt | D-Arg | Phe | Orn | NH$_2$ |
| 2'6'Dmt | D-Arg | Phe | Dab | NH$_2$ |
| 2'6'Dmt | D-Arg | Phe | Dap | NH$_2$ |
| 2'6'Dmt | D-Arg | Phe | Ahp(2-aminoheptanoic acid) | NH$_2$ |
| Bio-2'6'Dmt | D-Arg | Phe | Lys | NH$_2$ |
| 3'5'Dmt | D-Arg | Phe | Lys | NH$_2$ |
| 3'5'Dmt | D-Arg | Phe | Orn | NH$_2$ |
| 3'5'Dmt | D-Arg | Phe | Dab | NH$_2$ |
| 3'5'Dmt | D-Arg | Phe | Dap | NH$_2$ |
| Tyr | D-Arg | Tyr | Lys | NH$_2$ |
| Tyr | D-Arg | Tyr | Orn | NH$_2$ |
| Tyr | D-Arg | Tyr | Dab | NH$_2$ |
| Tyr | D-Arg | Tyr | Dap | NH$_2$ |
| 2'6'Dmt | D-Arg | Tyr | Lys | NH$_2$ |
| 2'6'Dmt | D-Arg | Tyr | Orn | NH$_2$ |
| 2'6'Dmt | D-Arg | Tyr | Dab | NH$_2$ |
| 2'6'Dmt | D-Arg | Tyr | Dap | NH$_2$ |
| 2'6'Dmt | D-Arg | 2'6'Dmt | Lys | NH$_2$ |
| 2'6'Dmt | D-Arg | 2'6'Dmt | Orn | NH$_2$ |
| 2'6'Dmt | D-Arg | 2'6'Dmt | Dab | NH$_2$ |
| 2'6'Dmt | D-Arg | 2'6'Dmt | Dap | NH$_2$ |
| 3'5'Dmt | D-Arg | 3'5'Dmt | Arg | NH$_2$ |
| 3'5'Dmt | D-Arg | 3'5'Dmt | Lys | NH$_2$ |
| 3'5'Dmt | D-Arg | 3'5'Dmt | Orn | NH$_2$ |
| 3'5'Dmt | D-Arg | 3'5'Dmt | Dab | NH$_2$ |
| Tyr | D-Lys | Phe | Dap | NH$_2$ |
| Tyr | D-Lys | Phe | Arg | NH$_2$ |
| Tyr | D-Lys | Phe | Lys | NH$_2$ |
| Tyr | D-Lys | Phe | Orn | NH$_2$ |
| 2'6'Dmt | D-Lys | Phe | Dab | NH$_2$ |
| 2'6'Dmt | D-Lys | Phe | Dap | NH$_2$ |
| 2'6'Dmt | D-Lys | Phe | Arg | NH$_2$ |
| 2'6'Dmt | D-Lys | Phe | Lys | NH$_2$ |
| 3'5'Dmt | D-Lys | Phe | Orn | NH$_2$ |
| 3'5'Dmt | D-Lys | Phe | Dab | NH$_2$ |
| 3'5'Dmt | D-Lys | Phe | Dap | NH$_2$ |
| 3'5'Dmt | D-Lys | Phe | Arg | NH$_2$ |
| Tyr | D-Lys | Tyr | Lys | NH$_2$ |
| Tyr | D-Lys | Tyr | Orn | NH$_2$ |
| Tyr | D-Lys | Tyr | Dab | NH$_2$ |
| Tyr | D-Lys | Tyr | Dap | NH$_2$ |
| 2'6'Dmt | D-Lys | Tyr | Lys | NH$_2$ |
| 2'6'Dmt | D-Lys | Tyr | Orn | NH$_2$ |
| 2'6'Dmt | D-Lys | Tyr | Dab | NH$_2$ |
| 2'6'Dmt | D-Lys | Tyr | Dap | NH$_2$ |
| 2'6'Dmt | D-Lys | 2'6'Dmt | Lys | NH$_2$ |
| 2'6'Dmt | D-Lys | 2'6'Dmt | Orn | NH$_2$ |
| 2'6'Dmt | D-Lys | 2'6'Dmt | Dab | NH$_2$ |
| 2'6'Dmt | D-Lys | 2'6'Dmt | Dap | NH$_2$ |
| 2'6'Dmt | D-Arg | Phe | dnsDap | NH$_2$ |
| 2'6'Dmt | D-Arg | Phe | atnDap | NH$_2$ |
| 3'5'Dmt | D-Lys | 3'5'Dmt | Lys | NH$_2$ |
| 3'5'Dmt | D-Lys | 3'5'Dmt | Orn | NH$_2$ |
| 3'5'Dmt | D-Lys | 3'5'Dmt | Dab | NH$_2$ |
| 3'5'Dmt | D-Lys | 3'5'Dmt | Dap | NH$_2$ |
| Tyr | D-Lys | Phe | Arg | NH$_2$ |
| Tyr | D-Orn | Phe | Arg | NH$_2$ |
| Tyr | D-Dab | Phe | Arg | NH$_2$ |
| Tyr | D-Dap | Phe | Arg | NH$_2$ |
| 2'6'Dmt | D-Arg | Phe | Arg | NH$_2$ |
| 2'6'Dmt | D-Lys | Phe | Arg | NH$_2$ |
| 2'6'Dmt | D-Orn | Phe | Arg | NH$_2$ |
| 2'6'Dmt | D-Dab | Phe | Arg | NH$_2$ |
| 3'5'Dmt | D-Dap | Phe | Arg | NH$_2$ |
| 3'5'Dmt | D-Arg | Phe | Arg | NH$_2$ |
| 3'5'Dmt | D-Lys | Phe | Arg | NH$_2$ |
| 3'5'Dmt | D-Orn | Phe | Arg | NH$_2$ |
| Tyr | D-Lys | Tyr | Arg | NH$_2$ |
| Tyr | D-Orn | Tyr | Arg | NH$_2$ |
| Tyr | D-Dab | Tyr | Arg | NH$_2$ |

TABLE 5-continued

Peptide Analogues with Mu-Opioid Activity

| Amino Acid Position 1 | Amino Acid Position 2 | Amino Acid Position 3 | Amino Acid Position 4 | C-Terminal Modification |
|---|---|---|---|---|
| Tyr | D-Dap | Tyr | Arg | NH$_2$ |
| 2'6'Dmt | D-Arg | 2'6'Dmt | Arg | NH$_2$ |
| 2'6'Dmt | D-Lys | 2'6'Dmt | Arg | NH$_2$ |
| 2'6'Dmt | D-Orn | 2'6'Dmt | Arg | NH$_2$ |
| 2'6'Dmt | D-Dab | 2'6'Dmt | Arg | NH$_2$ |
| 3'5'Dmt | D-Dap | 3'5'Dmt | Arg | NH$_2$ |
| 3'5'Dmt | D-Arg | 3'5'Dmt | Arg | NH$_2$ |
| 3'5'Dmt | D-Lys | 3'5'Dmt | Arg | NH$_2$ |
| 3'5'Dmt | D-Orn | 3'5'Dmt | Arg | NH$_2$ |
| Mmt | D-Arg | Phe | Lys | NH$_2$ |
| Mmt | D-Arg | Phe | Orn | NH$_2$ |
| Mmt | D-Arg | Phe | Dab | NH$_2$ |
| Mmt | D-Arg | Phe | Dap | NH$_2$ |
| Tmt | D-Arg | Phe | Lys | NH$_2$ |
| Tmt | D-Arg | Phe | Orn | NH$_2$ |
| Tmt | D-Arg | Phe | Dab | NH$_2$ |
| Tmt | D-Arg | Phe | Dap | NH$_2$ |
| Hmt | D-Arg | Phe | Lys | NH$_2$ |
| Hmt | D-Arg | Phe | Orn | NH$_2$ |
| Hmt | D-Arg | Phe | Dab | NH$_2$ |
| Hmt | D-Arg | Phe | Dap | NH$_2$ |
| Mmt | D-Lys | Phe | Lys | NH$_2$ |
| Mmt | D-Lys | Phe | Orn | NH$_2$ |
| Mmt | D-Lys | Phe | Dab | NH$_2$ |
| Mmt | D-Lys | Phe | Dap | NH$_2$ |
| Mmt | D-Lys | Phe | Arg | NH$_2$ |
| Tmt | D-Lys | Phe | Lys | NH$_2$ |
| Tmt | D-Lys | Phe | Orn | NH$_2$ |
| Tmt | D-Lys | Phe | Dab | NH$_2$ |
| Tmt | D-Lys | Phe | Dap | NH$_2$ |
| Tmt | D-Lys | Phe | Arg | NH$_2$ |
| Hmt | D-Lys | Phe | Lys | NH$_2$ |
| Hmt | D-Lys | Phe | Orn | NH$_2$ |
| Hmt | D-Lys | Phe | Dab | NH$_2$ |
| Hmt | D-Lys | Phe | Dap | NH$_2$ |
| Hmt | D-Lys | Phe | Arg | NH$_2$ |
| Mmt | D-Lys | Phe | Arg | NH$_2$ |
| Mmt | D-Orn | Phe | Arg | NH$_2$ |
| Mmt | D-Dab | Phe | Arg | NH$_2$ |
| Mmt | D-Dap | Phe | Arg | NH$_2$ |
| Mmt | D-Arg | Phe | Arg | NH$_2$ |
| Tmt | D-Lys | Phe | Arg | NH$_2$ |
| Tmt | D-Orn | Phe | Arg | NH$_2$ |
| Tmt | D-Dab | Phe | Arg | NH$_2$ |
| Tmt | D-Dap | Phe | Arg | NH$_2$ |
| Tmt | D-Arg | Phe | Arg | NH$_2$ |
| Hmt | D-Lys | Phe | Arg | NH$_2$ |
| Hmt | D-Orn | Phe | Arg | NH$_2$ |
| Hmt | D-Dab | Phe | Arg | NH$_2$ |
| Hmt | D-Dap | Phe | Arg | NH$_2$ |
| Hmt | D-Arg | Phe | Arg | NH$_2$ |

Dab = diaminobutyric

Dap = diaminopropionic acid

Dmt = dimethyltyrosine

Mmt = 2'-methyltyrosine

Tmt = N, 2',6'-trimethyltyrosine

Hmt = 2'-hydroxy,6'-methyltyrosine dnsDap = β-dansyl-L-α,β-diaminopropionic acid atnDap = β-anthraniloyl-L-α,β-diaminopropionic acid Bio = biotin Examples of peptides that do not activate mu-opioid receptors include, but are not limited to, the aromatic-cationic peptides shown in Table 6.

TABLE 6

Peptide Analogues Lacking Mu-Opioid Activity

| Amino Acid Position 1 | Amino Acid Position 2 | Amino Acid Position 3 | Amino Acid Position 4 | C-Terminal Modification |
|---|---|---|---|---|
| D-Arg | Dmt | Lys | Phe | $NH_2$ |
| D-Arg | Dmt | Phe | Lys | $NH_2$ |
| D-Arg | Phe | Lys | Dmt | $NH_2$ |
| D-Arg | Phe | Dmt | Lys | $NH_2$ |
| D-Arg | Lys | Dmt | Phe | $NH_2$ |
| D-Arg | Lys | Phe | Dmt | $NH_2$ |
| Phe | Lys | Dmt | D-Arg | $NH_2$ |
| Phe | Lys | D-Arg | Dmt | $NH_2$ |
| Phe | D-Arg | Phe | Lys | $NH_2$ |
| Phe | D-Arg | Dmt | Lys | $NH_2$ |
| Phe | D-Arg | Lys | Dmt | $NH_2$ |
| Phe | Dmt | D-Arg | Lys | $NH_2$ |
| Phe | Dmt | Lys | D-Arg | $NH_2$ |
| Lys | Phe | D-Arg | Dmt | $NH_2$ |
| Lys | Phe | Dmt | D-Arg | $NH_2$ |
| Lys | Dmt | D-Arg | Phe | $NH_2$ |
| Lys | Dmt | Phe | D-Arg | $NH_2$ |
| Lys | D-Arg | Phe | Dmt | $NH_2$ |
| Lys | D-Arg | Dmt | Phe | $NH_2$ |
| D-Arg | Dmt | D-Arg | Phe | $NH_2$ |
| D-Arg | Dmt | D-Arg | Dmt | $NH_2$ |
| D-Arg | Dmt | D-Arg | Tyr | $NH_2$ |
| D-Arg | Dmt | D-Arg | Trp | $NH_2$ |
| Trp | D-Arg | Phe | Lys | $NH_2$ |
| Trp | D-Arg | Tyr | Lys | $NH_2$ |
| Trp | D-Arg | Trp | Lys | $NH_2$ |
| Trp | D-Arg | Dmt | Lys | $NH_2$ |
| D-Arg | Trp | Lys | Phe | $NH_2$ |
| D-Arg | Trp | Phe | Lys | $NH_2$ |
| D-Arg | Trp | Lys | Dmt | $NH_2$ |
| D-Arg | Trp | Dmt | Lys | $NH_2$ |
| D-Arg | Lys | Trp | Phe | $NH_2$ |
| D-Arg | Lys | Trp | Dmt | $NH_2$ |
| Cha | D-Arg | Phe | Lys | $NH_2$ |
| Ala | D-Arg | Phe | Lys | $NH_2$ |

Cha = cyclohexyl alanine

The amino acids of the peptides shown in Table 5 and 6 may be in either the L- or the D-configuration.

Synthesis of the Peptides

The peptides may be synthesized by any of the methods well known in the art. Suitable methods for chemically synthesizing the protein include, for example, those described by Stuart and Young in *Solid Phase Peptide Synthesis*, Second Edition, Pierce Chemical Company (1984), and in *Methods Enzymol.*, 289, Academic Press, Inc, New York (1997).

Active Agents

The methods include the use of an aromatic-cationic peptide as described herein together with one or more additional therapeutic agents or active agents for the treatment of ischemia-reperfusion injury caused, for example by AMI or tissue or organ transplant. Thus, for example, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods described herein may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

In some embodiments, the combination therapy comprises administering to a subject in need thereof an aromatic-cationic peptide composition combined with an active agent selected from the group consisting of an angiotensin converting enzyme (ACE) inhibitor, a beta-blocker, a diuretic, an anti-arrhythmic agent, an anti-anginal agent, a tyrosine kinase receptor agonist, an anticoagulant, and a hypercholesterolemic agent.

In one embodiment, the active agent is an anti-arrhythmia agent. Anti-arrhythmia agents are often organized into four main groups according to their mechanism of action: type I, sodium channel blockade; type II, beta-adrenergic blockade; type III, repolarization prolongation; and type IV, calcium channel blockade. Type I anti-arrhythmic agents include lidocaine, lignocaine moricizine, mexiletine, tocainide, procainamide, encainide, flecanide, tocainide, phenytoin, propafenone, quinidine, disopyramide, and flecainide. Type II anti-arrhythmic agents include propranolol and esmolol. Type III includes agents that act by prolonging the duration of the action potential, such as amiodarone, artilide, bretylium, clofilium, isobutilide, sotalol, azimilide, dofetilide, dronedarone, ersentilide, ibutilide, tedisamil, and trecetilide. Type IV anti-arrhythmic agents include verapamil, diltaizem, digitalis, adenosine, nickel chloride, and magnesium ions. The effects of an exemplary anti-arrythmia agent in preventing or treating ischemia-reperfusion injury are described in Mohan et al., Cardioprotection by HO-4038, a novel verapamil derivative, targeted against ischemia and reperfusion-mediated acute myocardial infarction. *American Journal of Physiology—Heart & Circulatory Physiology.* 296(1): H140-51 (2009).

In one embodiment, the active agent is a vasodilator, for example, bencyclane, cinnarizine, citicoline, cyclandelate, cyclonicate, ebumamonine, hydralazine phenoxezyl, flunarizine, ibudilast, ifenprodil, lomerizine, naphlole, nikamate, nosergoline, nimodipine, papaverine, pentifylline, nofedoline, vincamin, vinpocetine, vichizyl, pentoxifylline, prostacyclin derivatives (such as prostaglandin E1 and prostaglandin I2), an endothelin receptor blocking drug (such as bosentan), diltiazem, nicorandil, and nitroglycerin. The effects of an exemplary vasodilator in preventing or treating ischemia-reperfusion injury are described in Garcia-Gonzalez, et al., New pharmacologic options in the treatment of acute coronary syndromes and myocardial ischemia-reperfusion injury: potential role of levosimendan. *Minerva Cardioangiologica.* 55(5): 625-35 (2007).

In one embodiment, the active agent is a anti-anginal agent, for example, nitrates, isosorbide nitrate, glyceryl trinitrate and pentaerythritol tetranitrate. The effects of an exemplary anti-anginal agent in preventing or treating ischemia-reperfusion injury are described in Kennedy et al., Effect of perhexiline and oxfenicine on myocardial function and metabolism during low-flow ischemia/reperfusion in the isolated rat heart. *Journal of Cardiovascular Pharmacology.* 36(6): 794-801 (2000).

In one embodiment, the active agent is a corticosteroid, such as hydrocortisone, hydrocortisone acetate, cortisone acetate, tixocortol pivalate, prednisolone, methylprednisolone, prednisone, triamcinolone acetonide, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate, and fluprednidene acetate. The effects of an exemplary corticosteroid in preventing or treating ischemia-reperfusion injury are described in Varas-Lorenzo et al., Use of oral corticosteroids and the risk of acute myocardial infarction. *Atherosclerosis.* 192(2): 376-83 (2007).

In one embodiment, the active agent is a cardioglycoside, for example, digoxin and digitoxin.

In one embodiment, the active agent is a diuretic, such as thiazide diuretics (such as hydrochlorothiazide, methyclothiazide, trichlormethiazide, benzylhydrochlorothiazide, and penflutizide), loop diuretics (such as furosemide, etacrynic acid, bumetanide, piretanide, azosemide, and torasemide), K sparing diuretics (spironolactone, triamterene, and potassium can renoate), osmotic diuretics (such as isosorbide, D-mannitol, and glycerin), nonthiazide diuretics (such as meticrane, tripamide, chlorthalidone, and mefruside), and acetazolamide. The effects of an exemplary diuretic in preventing or treating ischemia-reperfusion injury are described in Kasama et al., Effects of intravenous atrial natriuretic peptide on cardiac sympathetic nerve activity and left ventricular remodeling in patients with first anterior acute myocardial infarction. *Journal of the American College of Cardiology.* 49(6):667-74 (2007).

In one embodiment, the active agent is a sedative, for example, nitrazepam, flurazepam and diazepam. The effects of an exemplary sedative in preventing or treating ischemia-reperfusion injury are described in Lucchinetti et al., Sevoflurane inhalation at sedative concentrations provides endothelial protection against ischemia-reperfusion injury in humans. *Anesthesiology.* 106(2):262-268 (2007).

In one embodiment, the active agent is a cyclooxygenase inhibitor such as aspirin or indomethacin. In one embodiment, the cardiovascular agent is a platelet aggregation inhibitor such as clopidogrel, ticlopidene or aspirin. The effects of an exemplary cyclooxygenase inhibitor in preventing or treating ischemia-reperfusion injury are described in Bassuk et al., Non-selective cyclooxygenase inhibition before periodic acceleration (pGz) cardiopulmonary resuscitation (CPR) in a porcine model of ventricular fibrillation. *Resuscitation.* 77(2):250-7 (2008).

In one embodiment, the active agent is a angiotensin converting enzyme (ACE) inhibitor such as captopril, alacepril, lisinopril, imidapril, quinapril, temocapril, delapril, benazepril, cilazapril, trandolapril, enalapril, ceronapril, fosinopril, imadapril, mobertpril, perindopril, ramipril, spirapril, and randolapril, and salts of such compounds. The effects of an exemplary ACE inhibitor in preventing or treating ischemia-reperfusion injury are described in Kingma, J. H. and van Gilst, W. H., Angiotensin-converting enzyme inhibition during thrombolytic therapy in acute myocardial infarction: the Captopril and Thrombolysis Study (CATS). *Herz.* 18 Suppl 1:416-23 (1993).

In one embodiment, the active agent is an angiotensin II antagonist such as losartan, candesartan, valsartan, eprosartan, and irbesartan. The effects of an exemplary angiotensin II antagonist in preventing or treating ischemia-reperfusion injury are described in Moller et al., Effects of losartan and captopril on left ventricular systolic and diastolic function after acute myocardial infarction: results of the Optimal Trial in Myocardial Infarction with Angiotensin II Antagonist Losartan (OPTIMAAL) echocardiographic substudy. *American Heart Journal.* 147(3):494-501 (2004).

In one embodiment, the active agent is a thrombolytic agent such as tissue-type plasminogen activators (such as alteplase, tisokinase, nateplase, pamiteplase, monteplase, and rateplase), nasaruplase, streptokinase, urokinase, prourokinase, and anisoylated plasminogen streptokinase activator complex (APSAC, Eminase, Beecham Laboratories), aspirin, heparin, and Warfarin that inhibits Vit K-dependent factors, low molecular weight heparins that inhibit factors X and II, thrombin inhibitors, inhibitors of platelet GP IIbIIIa receptors, inhibitors of tissue factor (TF), inhibitors of human von Willebrand factor, reptilase, TNK-t-PA, staphylokinase, or animal salivary gland plasminogen activators. The effects of an exemplary thrombolytic agent in preventing or treating ischemia-reperfusion injury are described in Sikri, N. and Bardia, A., A history of streptokinase use in acute myocardial infarction. *Texas Heart Institute Journal.* 34(3):318-27 (2007).

In one embodiment, the active agent is a calcium channel blocking agent such as aranidipine, efonidipine, nicardipine, bamidipine, benidipine, manidipine, cilnidipine, nisoldipine, nitrendipine, nifedipine, nilvadipine, felodipine, amlodipine, diltiazem, bepridil, clentiazem, phendilin, galopamil, mibefradil, prenylamine, semotiadil, terodiline, verapamil, cilnidipine, elgodipine, isradipine, lacidipine, lercanidipine, nimodipine, cinnarizine, flunarizine, lidoflazine, lomerizine, bencyclane, etafenone, and perhexiline. The effects of an exemplary calcium channel blocking agent dilitazem in preventing or treating ischemia-reperfusion injury are described in Fansa et al., Does diltiazem inhibit the inflammatory response in cardiopulmonary bypass? *Medical Science Monitor.* 9(4):PI30-6 (2003).

In one embodiment, the active agent is a thromboxane receptor antagonist such as ifetroban, prostacyclin mimetics, or phosphodiesterase inhibitors. The effects of an exemplary thromboxane receptor antagonist in preventing or treating ischemia-reperfusion injury are described in Viehman et al., Daltroban, a thromboxane receptor antagonist, protects the myocardium against reperfusion injury following myocardial ischemia without protecting the coronary endothelium. *Methods & Findings in Experimental & Clinical Pharmacology.* 12(10):651-6 (1990).

In one embodiment, the active agent is a radical scavenger, such as edaravone, vitamin E, and vitamin C. The effects of an exemplary radical scavenger in preventing or treating ischemia-reperfusion injury are described in Higashi et al., Edaravone (3-methyl-1-phenyl-2-pyrazolin-5-one), a novel free radical scavenger, for treatment of cardiovascular diseases. *Recent Patents on Cardiovascular Drug Discovery.* 1(1):85-93 (2006).

In one embodiment, the active agent is a antiplatelet drug, such as ticlopidine hydrochloride, dipyridamole, cilostazol, ethyl icosapentate, sarpogrelate hydrochloride, dilazep hydrochloride, trapidil, a nonsteroidal antiinflammatory agent (such as aspirin), beraprostsodium, iloprost, and indobufene. The effects of an exemplary antiplatelet drug in preventing or treating ischemia-reperfusion injury are described in Ochiai et al., Impact of cilostazol on clinical and angiographic outcome after primary stenting for acute myocardial infarction. *American Journal of Cardiology.* 84(9):1074-6, A6, A9, (1999).

In one embodiment, the active agent is a β-adrenaline receptor blocking drug, such as propranolol, pindolol, indenolol, carteolol, bunitrolol, atenolol, acebutolol, metoprolol, timolol, nipradilol, penbutolol, nadolol, tilisolol, carvedilol, bisoprolol, betaxolol, celiprolol, bopindolol, bevantolol, labetalol, alprenolol, amosulalol, arotinolol, befunolol, bucumolol, bufetolol, buferalol, buprandolol, butylidine, butofilolol, carazolol, cetamolol, cloranolol, dilevalol, epanolol, levobunolol, mepindolol, metipranolol, moprolol, nadoxolol, nevibolol, oxprenolol, practol, pronetalol, sotalol, sufinalol, talindolol, tertalol, toliprolol, xybenolol, and esmolol. The effects of an exemplary β-adrenaline receptor blocking drug in preventing or treating ischemia-reperfusion injury are described in Kovacs et al., Prevalent role of Akt and ERK activation in cardioprotective effect of Ca(2+) channel- and beta-adrenergic receptor blockers. *Molecular & Cellular Biochemistry.* 321(1-2):155-164 (2009).

In one embodiment, the active agent is a α-receptor blocking drug, such as amosulalol, prazosin, terazosin, doxazosin, bunazosin, urapidil, phentolamine, arotinolol, dapiprazole, fenspiride, indoramin, labetalol, naftopidil, nicergoline, tamsulosin, tolazoline, trimazosin, and yohimbine. The effects of an exemplary α-receptor blocking drug in preventing or treating ischemia-reperfusion injury are described in Kim et al., Involvement of adrenergic pathways in activation of catalase by myocardial ischemia-reperfusion. *American Journal of Physiology—Regulatory Integrative & Comparative Physiology.* 282(5):R1450-1458, (2002).

In one embodiment, the active agent is an inotrope. Positive inotropic agents increase myocardial contractility, and are used to support cardiac function in conditions such as decompensated congestive heart failure, cardiogenic shock, septic shock, myocardial infarction, cardiomyopathy, etc. Examples of positive inotropic agents include, but are not limited to, Berberine, Bipyridine derivatives, Inamrinone, Milrinone, Calcium, Calcium sensitizers, Levosimendan, Cardiac glycosides, Digoxin, Catecholamines, Dopamine, Dobutamine, Dopexamine, Epinephrine (adrenaline), Isoprenaline (isoproterenol), Norepinephrine (noradrenaline), Eicosanoids, Prostaglandins, Phosphodiesterase inhibitors, Enoximone, Milrinone, Theophylline, and Glucagon. Negative inotropic agents decrease myocardial contractility, and are used to decrease cardiac workload in conditions such as angina. While negative inotropism may precipitate or exacerbate heart failure, certain beta blockers (e.g. carvedilol, bisoprolol and metoprolol) have been shown to reduce morbidity and mortality in congestive heart failure. Examples of negative inotropic agents include, but are not limited to, Beta blockers, Calcium channel blockers, Diltiazem, Verapamil, Clevidipine, Quinidine, Procainamide, disopyramide, and Flecainide.

In one embodiment, the active agent is a sympathetic nerve inhibitor, such as clonidine, guanfacine, guanabenz, methyldopa, and reserpine, hydralazine, todralazine, budralazine, and cadralazine. The effects of an exemplary sympathetic nerve inhibitor in preventing or treating ischemia-reperfusion injury are described in Chamberlain, D. A. and Vincent, R., Combined receptor intervention and myocardial infarction. *Drugs.* 28 Suppl 2:88-108, (1984).

In one embodiment, the active agent is a digitalis formulation (such as digitoxin, digoxin, methyldigoxin, deslanoside, vesnarinone, lanatoside C, and proscillaridin. The effects of an exemplary digitalis formulation in preventing or treating ischemia-reperfusion injury are described in Sanazaro, P. J., Use of deslanoside in acute myocardial infarction and cardiac emergencies: a probative agent for assessing digitalis saturation and for intramuscular digitalization. *American Practitioner & Digest of Treatment.* 8(12): 1933-41, (1957).

In one embodiment, the active agent is an antihyperlipidemic drug, such as atorvastatin, simvastatin, pravastatin sodium, fluvastatin sodium, clinofibrate, clofibrate, simfibrate, fenofibrate, bezafibrate, colestimide, and colestyramine. The effects of an exemplary antihyperlipidemic drug in preventing or treating ischemia-reperfusion injury are described in Ye et al., Enhanced cardioprotection against ischemia-reperfusion injury with a dipyridamole and low-dose atorvastatin combination. *American Journal of Physiology—Heart & Circulatory Physiology.* 293(1): H813-8 (2007).

In one embodiment, the active agent is an immunosuppressive agent. Exemplary immunosuppressive agents include, but are not limited to glucocorticoids, cytostatics, antibodies, drugs acting on immunophilins, and other drugs. Common immunosuppressive drugs used, e.g., to alleviate or prevent organ or tissue rejection after transplant include, but are not limited to cyclosporine, prednisone, azathioprine, tacrolimus or FK506, mycophenolate mofetil, sirolimus, and OKT3, as well as ATGAM and Thymoglobulin. In some embodiments, the active agent includes cyclosporine or functional derivatives or analogues thereof, such as NIM811.

Compositions Comprising an Aromatic-Cationic Peptide Linked to an Active Agent

In some embodiments, the compositions and methods described herein comprise aromatic-cationic peptides and cyclosporine joined to one another by means of a linker. The molecules may be linked by methods known in the art, such as, for example, by the addition of a cross linking agent. Non-limiting examples of cross-linking agents include dialdehydes, carbodiimides, dimaleimides, and the like. The order of addition of the molecules, peptides, and cross-linker is typically not important. For example, the peptide can be mixed with the cross-linker, followed by addition of an active agent such as cyclosporine. Alternatively, an active agent, such as cyclosporine can be mixed with the cross-linker, followed by addition of the peptide. Additionally or alternatively, the peptide and cyclosporine are mixed, followed by addition of the cross-linker.

In some embodiments, the linked peptide and cyclosporine are delivered to a cell. In some embodiments, the molecules functions in the cell without being cleaved from one another. In other instances, it may be beneficial to cleave the active agent, e.g., cyclosporine, from the aromatic cationic peptide. In some embodiments, the linkage may be cleavable by enzymes within the cell. Such enzymes include, but are not limited to proteases, esterases (see e.g., Vangapandu, S., et al., "8-Quinolinamines and their pro prodrug conjugates as potent blood-Schizontocidal antimalarial agents," 11(21) Bioorganic & Medicinal Chem. 4557-4568 (2003)), metalloproteases (see e.g., Patrick, A., et al., "Hydrogels for the detection and management of protease levels," 10(10) Macromol. Biosci. 1184-1193 (2010), noting that "[t]he peptide sequence GPQGIWGQ was used as the enzyme sensitive linker," and that "[t]his peptide sequence is cleavable by both MMP-1 and −12.33"), and β-glucosidase (see e.g., Sedlak, M., et al., "New targeting system for antimycotic drugs: β-Glucosidase sensitive Amphotericin B—star poly(ethylene glycol) conjugate," 18(9) Bioorganic & Medicinal Chem. Lett. 2952-2956 (2008)).

In some embodiments, aromatic-cationic peptides and cyclosporine are linked by means of a pH-sensitive linker such as hyrdozone (see e.g., Greenfield, R., et al., "Evaluation in Vitro of Adriamycin Immunoconjugates Synthesized Using an Acid-sensitive Hydrazone Linker," 50 Cancer Res. 660-6607 (1990)). Additional non-limiting examples of cleavable linkers include SMPT (i.e., 4succinimidyloxycarbonyl-ethyl-a-[2-pyridyldithio]toluene), Sulfo-LC-SPDP (i.e., sulfosuccinimidyl 6-(3-[2-pyridyldithio]- propionamido)hexanoate), LC-SPDP (i.e., succinimidyl 6-(3-[2-pyridyldithio]-propionamido)hexanoate), Sulfo-LC-SPDP (i.e., 20 sulfosuccinimidyL 6-(3-[2-pyridyldithio]-propionamido)hexanoate), SPDP (i.e., Nsuccinimidyl3-[2-pyridyldithio]-propionamidohexanoate), and AEDP (i.e., 3-[(2aminoethyl) dithio]propionic acid-HCl). In some embodiments, the composition comprises an active agent comprising cyclosporine, and the linked peptide comprises one or more of Tyr-D-Arg-Phe-Lys-NH$_2$; 2',6'-Dmt-D-Arg-Phe-Lys-NH$_2$; Phe-D-Arg-Phe-Lys-NH$_2$; 2',6'-Dmp-D-Arg-Phe-Lys-NH$_2$; and D-Arg-2',6'-Dmt-Lys-Phe-NH$_2$ or a pharmaceutically acceptable salt thereof, such as acetate salt or trifluoroacetate salt. In some embodiments, the composition comprises D-Arg-2',6'-Dmt-Lys-Phe-NH$_2$ (SS-31) or a pharmaceutically acceptable salt thereof, such as acetate salt or trifluoroacetate salt, linked by an enzymatically cleavable linker to cyclosporine.

Prophylactic and Therapeutic Uses of Aromatic-Cationic Peptides.

General. The aromatic-cationic peptides described herein are useful to prevent or treat disease or deleterious conditions related to ischemia-reperfusion injury. The combination of peptides and active agents described above are useful in treating any ischemia and/or reperfusion of a tissue or organ. Ischemia in a tissue or organ of a mammal is a multifaceted pathological condition which is caused by oxygen deprivation (hypoxia) and/or glucose (e.g., substrate) deprivation. Oxygen and/or glucose deprivation in cells of a tissue or organ leads to a reduction or total loss of energy generating capacity and consequent loss of function of active ion transport across the cell membranes. Oxygen and/or glucose deprivation also leads to pathological changes in other cell membranes, including permeability transition in the mitochondrial membranes. In addition other molecules, such as apoptotic proteins normally compartmentalized within the mitochondria, may leak out into the cytoplasm and cause apoptotic cell death. Profound ischemia can lead to necrotic cell death.

Ischemia or hypoxia in a particular tissue or organ may be caused by a loss or severe reduction in blood supply to the tissue or organ. The loss or severe reduction in blood supply may, for example, be due to transplantation (e.g., organ removal, transfer and introduction into a recipient), thromboembolic stroke, coronary atherosclerosis, or vascular disease or condition which limits blood flow to a tissue, an organ or a region of an organ. One non-limiting example of such a disease or condition is peripheral vascular disease. The tissue affected by ischemia or hypoxia is typically muscle, such as cardiac, skeletal, or smooth muscle. The organ affected by ischemia or hypoxia may be any organ that is subject to ischemia or hypoxia. Examples of organs affected by ischemia or hypoxia include brain, heart, lung, kidney, and prostate. For instance, cardiac muscle ischemia or hypoxia is commonly caused by atherosclerotic or thrombotic blockages which lead to the reduction or loss of oxygen delivery to the cardiac tissues by the cardiac arterial and capillary blood supply. Such cardiac ischemia or hypoxia may cause pain and necrosis of the affected cardiac muscle, and ultimately may lead to cardiac failure. Ischemia or hypoxia in skeletal muscle or smooth muscle may arise from similar causes. For example, ischemia or hypoxia in intestinal smooth muscle or skeletal muscle of the limbs may also be caused by atherosclerotic or thrombotic blockages. Any organs or tissues involved in a transplant procedure may also be affect by ischemia or hypoxia.

Reperfusion is the restoration of blood flow to any organ or tissue in which the flow of blood is decreased or blocked. For example, blood flow can be restored to any organ or tissue affected by ischemia or hypoxia. The restoration of blood flow (reperfusion) can occur by any method known to those in the art. For instance, reperfusion of ischemic cardiac tissues may arise from angioplasty, coronary artery bypass graft, or the use of thrombolytic drugs.

In some embodiments, a pharmaceutical composition comprising an aromatic-cationic peptide and a second active agent are administered to a subject suffering from ischemia and/or reperfusion injury of the brain, heart, lung, kidney, prostate, or other organ/tissue susceptible to ischemia and/or reperfusion injury. The aromatic-cationic peptide and a second active agent may be administered separately, sequentially, or simultaneously in effective amounts to reduce or ameliorate the effects of the ischemia and/or reperfusion injury of the brain, heart, lung, kidney, prostate, or other organ/tissue.

The disclosure also provides for both prophylactic and therapeutic methods of treating a subject at risk of (or susceptible to) vessel occlusion injury or cardiac ischemia-reperfusion injury. Accordingly, the present methods provide for the prevention and/or treatment of vessel occlusion injury or ischemia-reperfusion injury in a subject by administering an effective amount of an aromatic-cationic peptide or a pharmaceutically acceptable salt thereof such as acetate salt or trifluoroacetate salt, and one or more active agents such as cyclosporine to a subject in need thereof.

In various embodiments, suitable in vitro or in vivo assays are performed to determine the effect of a specific combination of aromatic-cationic peptides and one or more active agents and whether its administration is indicated for treatment. In various embodiments, in vitro assays can be performed with representative animal models to determine if a given aromatic-cationic peptide and cardiovascular agent treatment regime exerts the desired effect in preventing or treating ischemia-reperfusion injury. Compounds for use in therapy can be tested in suitable animal model systems including, but not limited to rats, mice, chicken, pigs, cows, monkeys, rabbits, and the like, prior to testing in human subjects. Similarly, for in vivo testing, any of the animal model systems known in the art can be used prior to administration to human subjects.

In one aspect, the invention provides a method for preventing, in a subject, acute myocardial infarction injury by administering to the subject an aromatic-cationic peptide and cyclosporine that prevents the initiation or progression of the condition. Subjects at risk for acute myocardial infarction injury can be identified by, e.g., any or a combination of diagnostic or prognostic assays as described herein. In prophylactic applications, pharmaceutical compositions or medicaments of aromatic-cationic peptides and cyclosporine are administered to a subject susceptible to, or otherwise at risk of a disease or condition in an amount sufficient to eliminate or reduce the risk, lessen the severity, or delay the outset of the disease, including biochemical, histologic and/or behavioral symptoms of the disease, its complications and intermediate pathological phenotypes presenting during development of the disease. Administration of a prophylactic aromatic-cationic and cyclosporine can occur prior to the manifestation of symptoms characteristic of the aberrancy, such that a disease or disorder is prevented or, alternatively, delayed in its progression. The appropriate compound can be determined based on screening assays described above.

Another aspect of the technology includes methods of treating vessel occlusion injury or cardiac ischemia-reperfusion injury in a subject for therapeutic purposes. In therapeutic applications, compositions or medicaments are administered to a subject suspected of, or already suffering from such a disease or conditions in an amount sufficient to cure, or at least partially arrest, the symptoms of the disease, including its complications and intermediate pathological phenotypes in development of the disease. As such, the invention provides methods of treating an individual afflicted with cardiac ischemia-reperfusion injury.

Treatment with aromatic-cationic peptides disclosed herein, such as D-Arg-2',6'-Dmt-Lys-Phe-NH$_2$ or pharmaceutically acceptable salts thereof such as acetate or trifluoroacetate, have been shown to be useful, inter alfa, to protect kidneys from acute renal injury (ARI). See e.g., U.S. patent application Ser. No. 12/392,565, herein incorporated by reference in its entirety. Another aspect of the technology includes methods of treating ischemia in any organ or tissue. For example, methods relate to the treatment of a condition in which kidneys (or other organs) fail to receive adequate blood supply (ischemia). Ischemia is a major cause of acute renal injury (ARI). Ischemia of one or both kidneys is a common problem experienced during aortic surgery, renal transplantation, or during cardiovascular anesthesia. Surgical procedures involving clamping of the aorta and/or renal arteries, e.g., surgery for supra- and juxtarenal abdominal aortic aneurysms and renal transplantation, are also particularly liable to produce renal ischemia, leading to significant postoperative complications and early allograft rejection. In high-risk patients undergoing these forms of surgery, the incidence of renal dysfunction has been reported to be as high as 50%. The skilled artisan will understand that the above described causes of ischemia are not limited to the kidney, but may occur in other organs undergoing surgical procedures. Accordingly, in some embodiments, such ischemia is treated, prevented, ameliorated (e.g., the severity of ischemia is decreased) by the administration of an aromatic-cationic peptide such as D-Arg-2',6'-Dmt-Lys-Phe-NH$_2$ or a pharmaceutically acceptable salt thereof, such as acetate or trifluoroacetate salt, and an active agent, such as cyclosporine or a derivative or analogue thereof.

Another aspect of the present technology includes methods for preventing or ameliorating cyclosporine-induced nephrotoxicity. For example, in some embodiments, a pharmaceutical composition or medicament comprising an aromatic-cationic peptide is administered to a subject presenting with or at risk of cyclosporine-induced nephrotoxicity. For example, in some embodiments, a subject receiving cyclosporine, e.g., as an immunosuppressant after an organ or tissue transplant, is also administered a therapeutically effective amount of an aromatic-cationic peptide. In some embodiments, the peptide is administered to the subject prior to organ or tissue transplant, during organ or tissue transplant and/or after an organ or tissue transplant. In some embodiments, the subject receives a combination of an aromatic-cationic peptide and cyclosporine before, during and/or after an organ or tissue transplant. The composition or medicament including the aromatic-cationic peptide and optionally, cyclosporine, is administered in an amount sufficient to cure, or at least partially arrest, the symptoms of nephrotoxicity, including its complications and intermediate pathological phenotypes. For example, in some embodiments, the compositions or medicaments are administered in an amount sufficient to eliminate the risk of, reduce the risk of, lessen the severity of, or delay the onset of nephrotoxicity, including biochemical, histologic and/or behavioral symptoms of the condition, its complications and intermediate pathological phenotypes. Administration of a prophylactic aromatic-cationic and cyclosporine can occur prior to the manifestation of symptoms characteristic of the aberrancy, such that the condition is prevented or, alternatively, delayed in its progression. Typically, subjects who receive the peptide will have a healthier transplanted organ or tissue, and/or will be able to maintain a higher and/or more consistent cyclosporine dosage or regiment for longer periods of time compared to subjects who do not receive the peptide. In some embodiments, patients receiving an aromatic-cationic peptide, such as D-Arg-2',6'-Dmt-Lys-Phe-NH$_2$ or a pharmaceutically acceptable salt thereof such as an acetate salt or a trifluoroacetate salt, in conjunction with cyclosporine will be able to tolerate longer and/or more consistent cyclosporine treatment regimens, and/or higher doses of cyclosporine. In some embodiments, patients receiving an aromatic-cationic peptide, such as D-Arg-2',6'-Dmt-Lys-Phe-NH$_2$ or a pharmaceutically acceptable salt thereof such as an acetate salt or a trifluoroacetate salt, in conjunction with cyclosporine, will have an increased tolerance for cyclosporine as compared to a patient who is not receiving the peptide.

Treatment with aromatic-cationic peptides disclosed herein, such as D-Arg-2',6'-Dmt-Lys-Phe-NH$_2$ have been shown to be useful, inter alfa, to decrease islet cell apoptosis and enhance viability of islet cells after transplantation. See e.g., U.S. Pat. Nos. 7,550,439 and 7,781,405 herein incorporated by reference in their entirety. Thus, another aspect of the present technology provides compositions and methods for organ and tissue preservation, for example, for transplant. For example, a removed organ can be susceptible to reperfusion injury due to lack of blood flow. Therefore, the aromatic-cationic peptides and active agents (e.g., cyclosporine or derivatives or analogues thereof) disclosed herein can be used to prevent reperfusion injury in the removed organ. For example, in some embodiments, pharmaceutical compositions or medicaments of aromatic-cationic peptides and cyclosporine are administered to a donor mammal prior to and/or during prolonged periods of ischemia such as would occur during preparation and removal of the organ or tissue for transplant. Additionally or alternatively, in some embodiments, the pharmaceutical compositions or medicaments of aromatic-cationic peptides and cyclosporine are administered to the removed organ. For example, in some embodiments, the removed organ is placed in a standard buffered solution, such as those commonly used in the art. For example, a removed heart can be placed in a cardioplegic solution containing the peptides and active agents described above. The concentration of peptide and active agent useful in the standard buffered solution can be easily determined by those skilled in the art. Such concentrations may be, for example, between about 0.1 nM to about 10 preferably about 1 µM to about 10 of peptide. Additionally or alternatively, in some embodiments, the pharmaceutical compositions or medicaments of aromatic-cationic peptides and cyclosporine are administered to the organ recipient. The compositions or medicaments are administered in an amount sufficient to eliminate, reduce the risk of, or lessen the severity of ischemia-reperfusion injury to the organ upon reperfusion.

Modes of Administration and Effective Dosages

Any method known to those in the art for contacting a cell, organ or tissue with a peptide and a one or more additional active agents may be employed. Suitable methods include in vitro, ex vivo, or in vivo methods. In vivo methods typically include the administration of an aromatic-cationic peptide and active agent, such as those described above, to a mammal, suitably a human. When used in vivo for therapy, the aromatic-cationic peptides and active agents are administered to the subject in effective amounts (i.e., amounts that have desired therapeutic effect). The dose and dosage regimen will depend upon the degree of the injury in the subject, the characteristics of the particular aromatic-cationic peptide used, e.g., its therapeutic index, the subject, and the subject's history. In some embodiments, the active agent comprises cyclosporine.

The effective amount may be determined during pre-clinical trials and clinical trials by methods familiar to physicians and clinicians. An effective amount of a peptide and active agent useful in the methods may be administered to a mammal in need thereof by any of a number of well-known methods for administering pharmaceutical compounds. For example, in some embodiments, the peptide and the additional active agent may be administered systemically or locally.

The compound may be formulated as a pharmaceutically acceptable salt. The term "pharmaceutically acceptable salt" means a salt prepared from a base or an acid which is acceptable for administration to a patient, such as a mammal (e.g., salts having acceptable mammalian safety for a given dosage regime). However, it is understood that the salts are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a peptide contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucoronic, mandelic, mucic, nicotinic, orotic, pamoic, pantothenic, sulfonic acids (e.g., benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like. In some embodiments, the pharmaceutically acceptable salt comprises acetate salt or trichloroacetate salt.

The compounds described herein can be incorporated into pharmaceutical compositions for administration, singly or in combination, to a subject for the treatment or prevention of a disorder described herein. In some embodiments, such compositions typically include the active agents (e.g., peptide and cyclosporine) and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment (e.g., vials of drug, vials of diluent, syringes and needles) for a treatment course (e.g., 7 days of treatment).

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

The pharmaceutical compositions can include a carrier, which can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compounds can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressurized container or dispenser which contains a suitable propellant, e.g., a gas such as carbon dioxide, or a nebulizer. Such methods include those described in U.S. Pat. No. 6,468,798.

Systemic administration of a therapeutic composition as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In one embodiment, transdermal administration may be performed by iontophoresis.

A therapeutic composition can be formulated in a carrier system. The carrier can be a colloidal system. The colloidal system can be a liposome, a phospholipid bilayer vehicle. In one embodiment, the therapeutic peptide is encapsulated in a liposome while maintaining peptide integrity. As one skilled in the art would appreciate, there are a variety of methods to prepare liposomes. (See Lichtenberg et al., *Methods Biochem. Anal.*, 33:337-462 (1988); Anselem et al., *Liposome Technology*, CRC Press (1993)). Liposomal formulations can delay clearance and increase cellular uptake (See Reddy, *Ann. Pharmacother.*, 34(7-8):915-923 (2000)). An active agent can also be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

The carrier can also be a polymer, e.g., a biodegradable, biocompatible polymer matrix. In one embodiment, the therapeutic peptide can be embedded in the polymer matrix, while maintaining protein integrity. The polymer may be natural, such as polypeptides, proteins or polysaccharides, or synthetic, such as poly α-hydroxy acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect. (See Reddy, *Ann. Pharmacother.*, 34(7-8):915-923 (2000)). A polymer formulation for human growth hormone (hGH) has been used in clinical trials. (See Kozarich and Rich, *Chemical Biology*, 2:548-552 (1998)).

Examples of polymer microsphere sustained release formulations are described in PCT publication WO 99/15154 (Tracy et al.), U.S. Pat. Nos. 5,674,534 and 5,716,644 (both to Zale et al.), PCT publication WO 96/40073 (Zale et al.), and PCT publication WO 00/38651 (Shah et al.). U.S. Pat. Nos. 5,674,534 and 5,716,644 and PCT publication WO 96/40073 describe a polymeric matrix containing particles of erythropoietin that are stabilized against aggregation with a salt.

In some embodiments, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylacetic acid. Such formulations can be prepared using known techniques. The materials can also be obtained commercially, e.g., from Alza Corporation and Nova Pharmaceuticals, Inc. Liposomal suspensions (including liposomes targeted to specific cells with monoclonal antibodies to cell-specific antigens) can also be used as pharmaceutically acceptable carriers. These can be prepared according to methods known to those skilled in the art, for example, as described in U.S. Pat. No. 4,522,811.

The therapeutic compounds can also be formulated to enhance intracellular delivery. For example, liposomal delivery systems are known in the art, see, e.g., Chonn and Cullis, "Recent Advances in Liposome Drug Delivery Systems," *Current Opinion in Biotechnology* 6:698-708 (1995); Weiner, "Liposomes for Protein Delivery: Selecting Manufacture and Development Processes," *Immunomethods*, 4(3): 201-9 (1994); and Gregoriadis, "Engineering Liposomes for Drug Delivery: Progress and Problems," *Trends Biotechnol.*, 13(12):527-37 (1995). Mizguchi et al., *Cancer Lett.*, 100: 63-69 (1996), describes the use of fusogenic liposomes to deliver a protein to cells both in vivo and in vitro.

Dosage, toxicity and therapeutic efficacy of the therapeutic agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In some embodiments, an effective amount of the aromatic-cationic peptides and/or an additional active agent such as cyclosporine sufficient for achieving a therapeutic or prophylactic effect, range from about 0.000001 mg per kilogram body weight per day to about 10,000 mg per kilogram body weight per day. Preferably, the dosage ranges are from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In one embodiment, a single dosage of peptide ranges from 0.1-10,000 micrograms per kg body weight. In one embodiment, aromatic-cationic peptide concentrations in a carrier range from 0.2 to 2000 micrograms per delivered milliliter.

In some embodiments, a therapeutically effective amount of an aromatic-cationic peptide may be defined as a concentration of peptide at the target tissue of 10 to 10 molar, e.g., approximately 10 molar. This concentration may be delivered by systemic doses of 0.01 to 100 mg/kg or equivalent dose by body surface area. The schedule of doses would be optimized to maintain the therapeutic concentration at the target tissue, most preferably by single daily or weekly administration, but also including continuous administration (e.g., parenteral infusion or transdermal application).

In some embodiments, the dosage of the aromatic-cationic peptide is provided at a "low," "mid," or "high" dose level. In one embodiment, the low dose is provided from about 0.0001 to about 0.5 mg/kg/h, from about 0.01 to about 0.5 mg/kg/h, suitably from about 0.001 to about 0.1 mg/kg/h or from about or 0.01 to about 0.1 mg/kg/h. In one embodiment, the mid-dose is provided from about 0.01 to about 1.0 mg/kg/h, from about 0.1 to about 1.0 mg/kg/h, suitably from about 0.01 to about 0.5 mg/kg/h or from about 0.1 to about 0.5 mg/kg/h. In one embodiment, the high dose is provided from about 0.5 to about 10 mg/kg/h, suitably from about 0.5 to about 2 mg/kg/h. In an illustrative embodiment, the dose of active agent is from about 1 to 100 mg/kg, suitably about 25 mg/kg. In some embodiments, the active agent comprises cyclosporine.

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

The mammal treated in accordance present methods can be any mammal, including, for example, farm animals, such as sheep, pigs, cows, and horses; pet animals, such as dogs and cats; laboratory animals, such as rats, mice and rabbits. In a preferred embodiment, the mammal is a human.

Also disclosed herein are kits. In some embodiments, a kit for treating an acute myocardial infarction injury in a mammalian subject is provided. In other embodiments, a kit for treating ischemia and/or reperfusion injury in a subject in need thereof is provided. In still other embodiments, a kit for preventing or reducing ischemia-reperfusion injury in a removed organ of a mammal is provided. In further embodiments, a kit for the treatment, prevention or alleviation of symptoms of cyclosporine-induced nephrotoxicity in a subject in need thereof is provided. Typically, the kits include (i) an aromatic-cationic peptide or a pharmaceutically acceptable salt thereof, and (ii) one or more additional active agents. In some embodiment, the aromatic-cationic peptide is selected from the group consisting of: Tyr-D-Arg-Phe-Lys-NH$_2$; 2',6'-Dmt-D-Arg-Phe-Lys-NH$_2$; Phe-D-Arg-Phe-Lys-NH$_2$; 2',6'-Dmp-D-Arg-Phe-Lys-NH$_2$; and D-Arg-2',6'-Dmt-Lys-Phe-NH$_2$ or a pharmaceutically acceptable salt thereof, such as an acetate salt or a trifluoroacetate salt. In some embodiments, the additional active agent comprises cyclosporine. In some embodiments, the kit comprises D-Arg-2'6'-Dmt-Lys-Phe-NH$_2$ or a pharmaceutically acceptable salt thereof selected from acetate salt or trifluoroacetate salt, and cyclosporine. In some embodiments, the peptide and the one or more additional active agents, such as cyclosporine, are packaged in the same or separate vials. In some embodiments, instructions for administering the components of the kit are also provided.

EXAMPLES

The present invention is further illustrated by the following example, which should not be construed as limiting in any way.

Example 1. Effects of an Aromatic-Cationic Peptide in Protecting Against Acute Myocardial Infarction Injury in a Rabbit Model The effects of aromatic-cationic peptides in protecting against an acute myocardial infarction injury in a rabbit model were investigated. The myocardial protective effect of the peptide D-Arg-2'6'-Dmt-Lys-Phe-NH$_2$ were demonstrated by this Example.

New Zealand white rabbits were used in this study. The rabbits were males and >10 weeks in age. Environmental controls in the animal rooms were set to maintain temperatures of 61° to 72° F. and relative humidity between 30% and 70%. Room temperature and humidity were recorded hourly, and monitored daily. There were approximately 10-15 air exchanges per hour in the animal rooms. Photoperiod was 12-hr light/12-hr dark (via fluorescent lighting) with exceptions as necessary to accommodate dosing and data collection. Routine daily observations were performed. Harlan Teklad, Certified Diet (2030C), rabbit diet was provided approximately 180 grams per day from arrival to the facility. In addition, fresh fruits and vegetables were given to the rabbit 3 times a week.

The peptide D-Arg-2'6'-Dmt-Lys-Phe-NH$_2$ (sterile lyophilized powder) was used as the test article. Dosing solutions were formulated at no more than 1 mg/ml, and were delivered via continuous infusion (IV) at a constant rate (e.g., 50 µL/kg/min). Normal saline (0.9% NaCl) was used as a control.

The test/vehicle articles were given intravenously, under general anesthesia, in order to mimic the expected route of administration in the clinical setting of AMI and PTCA. Intravenous infusion was administered via a peripheral vein using a Kd Scientific infusion pump (Holliston, Mass. 01746) at a constant volume (e.g., 50 µL/kg/min).

The study followed a predetermined placebo and sham controlled design. In short, 10-20 healthy, acclimatized, male rabbits were assigned to one of three study arms (approximately 2-10 animals per group). Arm A (n=4, CTRL/PLAC) includes animals treated with vehicle (vehicle; VEH, IV); Arm B (n=7, treated) includes animals treated with peptide; Arm C (n=2, SHAM) includes sham-operated time-controls treated with vehicle (vehicle; VEH, IV) or peptide.

TABLE 7

Study Design.

| Group | Study Group | Ischemia Time | Reperfusion Time |
|---|---|---|---|
| A | CONTROL/PLACEBO | 30 Min (Last 20 Min. With Placebo) | 180 Min of Placebo |
| B | PEPTIDE | 30 Min (Last 20 Min. With Peptide) | 180 Min of Peptide |
| C | SHAM (FOR SURGERY WITHOUT ISCHEMIA) | 0 Min (Last 20 Min. With Placebo) | 180 Min of Placebo (Vehicle) or Peptide |

In all cases, treatments were started approximately 30 min after the onset of a 30 min ischemic insult (coronary occlusion) and continued for up to 3 h following reperfusion. In all cases, cardiovascular function was monitored both prior to and during ischemia, as well as for up to 180 min (3 h) post-reperfusion. The experiments were terminated 3 h post-reperfusion (end of study); irreversible myocardial injury (infarct size by histomorphometery) at this time-point was evaluated, and was the primary-end-point of the study. The study design is summarized in Table 7.

Anesthesia/Surgical Preparation.

General anesthesia was induced intramuscularly (IM) with a ketamine (~35-50 mg/kg)/xylazine (~5-10 mg/kg) mixture. A venous catheter was placed in a peripheral vein (e.g., ear) for the administration of anesthetics. In order to preserve autonomic function, anesthesia was maintained with continuous infusions of propofol (~8-30 mg/kg/hour) and ketamine (~1.2-2.4 mg/kg/hr). A cuffed tracheal tube was placed via a tracheotomy (ventral midline incision) and used to mechanically ventilate the lungs with a 95% O$_2$/5% CO$_2$ mixture via a volume-cycled animal ventilator (~40 breaths/minute with a tidal volume of ~12.5 ml/kg) in order to sustain PaCO$_2$ values broadly within the physiological range.

Once a surgical plane of anesthesia was reached, either transthoracic or needle electrodes forming two standard ECG leads (e.g., lead II, aVF, V2) were placed. A cervical cut-down exposed a carotid artery, which was isolated, dissected free from the surrounding tissue and cannulated with a dual-sensor high-fidelity micromanometer catheter (Millar Instruments); the tip of this catheter was advanced into the left-ventricle (LV) retrogradely across the aortic valve, in order to simultaneously determine aortic (root, proximal transducer) and left-ventricular (distal transducer) pressures. The carotid cut-down also exposed the jugular vein, which was cannulated with a hollow injection catheter (for blood sampling). Finally, an additional venous catheter was placed in a peripheral vein (e.g., ear) for the administration of vehicle/test articles.

Subsequently, the animals were placed in right-lateral recumbence and the heart was exposed via a midline thoracotomy and a pericardiotomy. The heart was suspended on a pericardial cradle in order to expose the left circumflex (LCX) and the left-anterior descending (LAD) coronary arteries. Silk ligatures were loosely placed (using a taper-point needle) around the proximal LAD and if necessary, depending on each animal's coronary anatomy, around one or more branches of the LCX marginal coronary arteries. Tightening of these snares (via small pieces of polyethylene tubing) allowed rendering a portion of the left ventricular myocardium temporarily ischemic.

Once instrumentation was completed, hemodynamic stability and proper anesthesia depth were verified/ensured for at least 30 min. Subsequently, the animals were paralyzed with atracurium (~0.1 to 0.2 mg/kg/hr IV) in order to facilitate hemodynamic/respiratory stability. Following atracurium administration, signs of autonomic hyperactivity and/or changes in BIS values were used to evaluate anesthesia depth and/or to up-titrate the intravenous anesthetics.

Experimental Protocol/Cardiovascular Data Collection.

Immediately following surgical preparation, the animals were heparinized (100 units heparin/kg/h, IV bolus), and after hemodynamic stabilization (for approximately 30 min), baseline data were collected including venous blood for the evaluation of cardiac enzymes/biomarkers as well as of test-article concentrations.

Following hemodynamic stabilization and baseline measurements, the animals were subjected to an acute 60 min ischemic insult by tightening of the LAD/LCX coronary artery snares. Myocardial ischemia was visually confirmed by color (i.e., cyanotic) changes in distal distributions of the LAD/LCX and by the onset of electrocardiographic changes. Approximately after 10 min of ischemia, the animals received a continuous infusion of either vehicle (saline) or peptide; ischemia was continued for a additional 20 min (i.e., 30 min total) after the start of treatment. Subsequently (i.e., after 30 min of ischemia of which the last 20 min overlap with the treatment), the coronary snares were released and the previously ischemic myocardium was reperfused for up to 3 h. Treatment with either vehicle or peptide was continued throughout the reperfusion period. It should be noted that in sham-operated animals the vessel snares were manipulated at the time of ischemia/reperfusion onset, but were not either tightened or loosened.

Cardiovascular data collection occurred at 11 pre-determined time-points: post-instrumentation/stabilization (i.e., baseline), after 10 and 30 min of ischemia, as well as at 5, 15, 30, 60, 120, and 180 min post-reperfusion. Throughout the experiments, analogue signals were digitally sampled (1000 Hz) and recorded continuously with a data acquisition system (IOX; EMKA Technologies), and the following parameters were determined at the above-mentioned time-points: (1) from bipolar transthoracic ECG (e.g., Lead II, aVF): rhythm (arrhythmia quantification/classification), RR, PQ, QRS, QT, QTc, short-term QT instability, and QT:TQ (restitution); (2) from solid-state manometer in aorta (Millar): arterial/aortic pressure (AoP); and (3) from solid-state manometer in the LV (Millar): left-ventricular pressures (ESP, EDP) and derived indices (dP/dtmax, dP/dtmin, Vmax, and tau). In addition, in order to determine/quantify the degree of irreversible myocardial injury (i.e., infarction) resulting from the I/R insult with and without peptide treatment, cardiac biomarkers as well as infarct area were evaluated.

Blood Samples.

Venous (<3 mL) whole blood samples were collected for both pharmaco-kinetic (PK) analysis as well as for the evaluation of myocardial injury via cardiac biomarker analyses at six data-collection time-points: baseline, 30 min of ischemia, as well as 30, 60, 120 and 180 min post-reperfusion. Two clinically used biomarkers were measured: cardiac Troponin-I (cTnI) and creatine-kinase (CK-MB). In addition, three arterial (~0.5 mL) whole blood samples were collected at baseline, 60 min of ischemia, as well as the 60 and 180 min post-reperfusion for the determination of blood-gases; the arterial samples were collected into blood gas syringes and used for the measurement of blood-gases via an I-Stat analyzer/cartridges (CG4+).

Histopathology/Histomorphometery.

At the completion of the protocol, irreversible myocardial injury (i.e., infarction) resulting from the FR insult was evaluated. In short, the coronary snares were retightened and Evan's blue dye (1 mL/kg; Sigma, St. Louis, Mo.) was injected intravenously to delineate the myocardial area-at-risk (AR) during ischemia. Approximately 5 min later, the heart was arrested (by an injection of potassium chloride into the left atrium), and freshly excised. The LV was sectioned perpendicular to its long axis (from apex to base) into 3 mm thick slices. Subsequently, the slices were incubated for 20 min in 2% triphenyl-tetrazolium-chloride (TTC) at 37° C. and fixed in a 10% non-buffered formalin solution (NBF).

Following fixation, the infarct and at-risks areas were delineated/measured digitally. For such purpose, the thickness of each slice was measured with a digital micrometer and later photographed/scanned. All photographs were imported into an image analysis program (Image J; National Institutes of Health), and computer-assisted planometry was performed to determine the overall size of the infarct (I) and at-risk (AR) areas. For each slide, the AR (i.e., not stained blue) was expressed as a percentage of the LV area, and the infarct size (I, not stained tissue) was expressed as a percentage of the AR (I/AR). In all cases, quantitative histo-morphometery was performed by personnel blinded to the treatment assignment/study-design.

Animal Observations.

Data were acquired on the EMKA's IOX system using ECG Auto software for analysis (EMKA Technologies). Measurements for all physiological parameters were made manually or automatically from (digital) oscillograph tracings. The mean value from 60 s of data from each targeted time point was used (if possible); however, as mentioned above, signals/tracing was recorded continuously throughout the experiments, in order to allow (if needed) more fine/detailed temporal data analysis (via amendments). Additional calculations were performed using Microsoft Excel. Data is presented as means with standard errors.

Administration of peptide resulted in decreased infarct size compared to the control. Table 8 presents data showing the ratios of area of risk to left ventricular area infracted area to left ventricular area, and infracted area to area of risk for each of the animals used in this study.

TABLE 8

Histopathology Results of Study Animals

| Animal ID | Group | IA/LV | AR/LV | IA/AR | Group Mean IA/AR | Percent Difference in IA/AR from Placebo |
|---|---|---|---|---|---|---|
| A-1 | SHAM | 1.5% | 55.6% | 2.5% | 2.8% | −93.0% |
| A-2 | | 1.9% | 56.3% | 3.1% | | |
| B-1 | PEPTIDE TREATED | 4.3% | 53.6% | 7.3% | 16.2 | −59.0 |
| B-2 | | 10.5% | 57.2% | 17.2% | | |
| B-3 | | 8.1% | 56.7% | 12.8% | | |
| B-4 | | 6.7% | 44.6% | 13.8% | | |
| B-5 | | 8.3% | 56.2% | 13.8% | | |
| B-6 | | 13.3% | 61.8% | 19.7% | | |
| B-7 | | 20.5% | 65.3% | 28.6% | | |
| C-1 | PLACEBO | 20.6% | 54.9% | 34.5% | 39.1% | 0.0% |
| C-2 | | 23.6% | 60.5% | 35.1% | | |
| C-3 | | 25.6% | 62.8% | 39.9% | | |
| C-4 | | 31.9% | 64.3% | 46.7% | | |

These results show that in a standardized rabbit model of acute myocardial ischemia and reperfusion, peptide when administered as an IV continuous infusion beginning at 10 min into a 30 min ischemia period followed by IV continuous infusion for 180 min after reperfusion was able to reduce myocardial infarct size compared to the control group. In the rabbits in which there was a definable response to treatment, the size of the myocardial infarct area was reduced by 59% relative to the infarct size noted in control animals. These results indicate that peptide treatment prevents the occurrence of symptoms of acute cardiac ischemia-reperfusion injury. As such, aromatic-cationic peptides are useful in methods at preventing and treating a acute myocardial infarction injury in mammalian subjects.

Example 2. Effects of Intravenous Cyclosporine Treatment After Ischemia in a Rabbit Model of Acute Myocardial Infarction Experimental studies suggest that pretreatment with cyclosporine-A (CsA) can attenuate/mitigate myocardial injury resulting from an ischemia/reperfusion (FR) insult as can occur clinically following acute myocardial infarction (AMI) and/or Percutaneous Coronary Intervention/Angioplasty (PCI). A 1-hour intravenous infusion of CsA (25 mg/kg) prior to the onset of ischemia reduced the resulting infarct size significantly when compared against control. CsA (2.5 mg/kg IV bolus), when given just prior to the onset of reperfusion, may also have myocardial sparing effects. This study is designed to test the cardioprotective effects of CsA in a setting that mimics the clinical scenario of an acute FR insult. The study will be conducted under the general hypothesis that treatment with CsA after the onset of ischemia (but prior to reperfusion) will attenuate irreversible myocardial injury (i.e., infarct size) and preserve myocardial function.

Both vehicle and cyclosporine-A (CsA) will be administered via a slow intravenous infusion (0.5 mL/min) during/following a 30-min ischemic insult, starting 20 min prior to the onset of reperfusion, and ending 20 min after reperfusion. The test article is cyclosporine injection, USP (cyclosporine-A, CsA). One vial (50 mg/mL, 5 mL) of the clinical CsA formulation for injection will be maintained at room temperature for 30 min before formulation. Subsequently, the appropriate amount of test article (25 mg/kg) will be dissolved in the sterile vehicle (see below; Hespan, 6% Hetastarch in 0.9% Sodium Chloride. The test/vehicle articles will be given intravenously, under general anesthesia, in order to mimic the expected route of administration in the clinical setting of AMI and PTCA. Intravenous infusion will be administered via a peripheral vein using a Kd Scientific infusion pump (Holliston, Mass. 01746) at a constant time/volume (20 mL over 40 min, or 500 uL/min).

The study will follow a pre-determined placebo controlled design. In short, healthy, acclimatized, male rabbits will be assigned to one of three study arms:

1. Arm A (n<=6, CTRL): treated with vehicle (vehicle; VEH, IV).
2. Arm B (n<=6, CsA): treated with CsA (25 mg/kg, IV continuous infusion).
3. Arm C (n<=6, SHAM): sham-operated time-controls treated with CsA (25 mg/kg intravenous bolus infusion).

TABLE 9

Study Design.

| ARM | I/R PERIOD (min) | INTERVENTION |
|---|---|---|
| CTRL (n <= 6) | 30/180 | Placebo/Vehicle (for CsA) Cont. 40 min infusion beginning at +10 min of ischemia (i.e., lasting 20 min into reperfusion) |
| CsA (n <= 6) | 30/180 | CsA Cont. 40 min infusion beginning at +10 min of ischemia (i.e., lasting 20 min into reperfusion) |
| SHAM (n <= 6) | 0/0 | CsA Cont. 40 min infusion beginning at +10 min of ischemia (i.e., lasting 20 min into reperfusion) |

In all cases, treatments will be started approximately 10 min after the onset of a 30 min ischemic insult (coronary occlusion) and continued for only 20 min following reperfusion. In all cases, cardiovascular function will be monitored both prior to and during ischemia, as well as for up to 180 minutes (3 hours) post-reperfusion. The experiments will be terminated 3 hours post-reperfusion (end of study); irreversible myocardial injury (infarct size by histomorphometry) at this time-point will be evaluated, and will be the primary-end-point of the study. The study design is summarized in Table 9 (above).

Anesthesia/Surgical Preparation.

General anesthesia will be induced intramuscularly (IM) with a ketamine (~35-50 mg/kg)/xylazine (~5-10 mg/kg) mixture. A venous catheter will be placed in a peripheral vein (e.g., ear) for the administration of anesthetics. In order to preserve autonomic function, anesthesia will be maintained with continuous infusions of propofol (~8-30 mg/kg/hour) and (if necessary) ketamine (~1.2-2.4 mg/kg/hr). A cuffed tracheal tube will be placed via a tracheotomy (ventral midline incision) and used to mechanically ventilate the lungs with a 100% $O_2$ via a volume-cycled animal ventilator (~40 breaths/minute with a tidal volume of ~12.5 ml/kg) in order to sustain $PaCO_2$ values within the physiological range.

Once a surgical plane of anesthesia has been reached, either transthoracic or needle electrodes forming two standard ECG leads (e.g., lead II, aVF, V2) will be placed. A cervical cut-down will expose a carotid artery, which will be isolated, dissected free from the surrounding tissue and cannulated with a dual-sensor high-fidelity micromanometer catheter (Millar Instruments); the tip of this catheter will be advanced into the left-ventricle (LV) retrogradely across the aortic valve, in order to simultaneously determine aortic (root, proximal transducer) and left-ventricular (distal transducer) pressures. The carotid cut-down will also expose the jugular vein, which will be cannulated with a hollow injection catheter (for blood sampling). Finally, an additional venous catheter will be placed in a peripheral vein (e.g., ear) for the administration of vehicle/test articles.

Subsequently, the animals will be placed in dorsal recumbence and the heart will be exposed via a midline sternotomy and a pericardiotomy. The heart will be suspended on a pericardial cradle in order to expose the left circumflex (LCX) and the left-anterior descending (LAD) coronary arteries. Silk ligatures will be loosely placed (using a taper-point needle) approximately at the midpoint of the LCX artery (i.e., midpoint between its origin and the cardiac apex), and if necessary (depending on each animal's coronary anatomy), around either the proxima//distal LAD or one of its branches (e.g., 1st. diagonal). Tightening of these snares (via small pieces of polyethylene tubing) will allow rendering a portion of myocardium temporarily ischemic. In order to prevent/minimize premature mortality resulting from ischemic arrhythmias (i.e., Class I), the animals may receive prophylactic anti-arrhythmic therapy prior to the coronary occlusion (lidocaine HCl 2 mg/kg iv, bolus).

Once instrumentation has been completed and proper anesthesia depth verified/ensured for at least 30 min, the animals may be paralyzed with atracurium (~0.1 to 0.2 mg/kg/hr IV) in order to facilitate hemodynamic and respiratory stability. However, it should be highlighted that prior to the administration of this muscle relaxant, adequacy of the anesthetic plane will be carefully monitored (and the anesthetic regimen titrated) using somatic as well as autonomic signs for assessing anesthesia depth, paying particular attention to muscle tone and ventilatory pattern; hemodynamic (mean arterial pressure, heart rate, etc.) stability (for ~30 min) at a given (fixed) anesthetic regimen, will be required prior to the administration of atracurium. In addition, in order to aid with the establishment/maintenance of a proper anesthetic plane, the Bispectral Index (BIS), a numerical value derived from the electroencephalogram (EEG) indicating the level of consciousness will be continuously monitored. Following atracurium administration, signs of autonomic hyperactivity and/or changes in BIS values will be used to evaluate anesthesia depth and/or to up-titrate the intravenous anesthetics.

Experimental Protocol/Cardiovascular Data Collection.

Immediately following surgical preparation, the animals will be heparinized (100 units heparin/kg/hour, IV bolus), and after hemodynamic stabilization (for approximately 30 min), baseline data will be collected including venous blood for the evaluation of cardiac enzymes/biomarkers as well as of test-article concentrations (see below). It should be noted that in order to ensure experimental/data homogeneity, all animals must satisfy the following entry criteria: dP/dt-max>1000 mmHg/s; the anesthetic regime may be adjusted in order to ensure proper anesthesia/analgesia and to satisfy such inclusion criteria. Additionally, in order to ensure an adequate intravascular volume status and cardiovascular hemodynamics at baseline, a physiologic volume expander (vehicle, 6% hetastarch in 0.9% sodium chloride) may be administered.

Following hemodynamic stabilization and baseline measurements, the animals will be subjected to an acute 30 min ischemic insult by tightening of the LCX/LAD coronary artery snares. Myocardial ischemia will be visually confirmed by color (i.e., cyanotic) changes in distal distributions of the LCX/LAD and by the onset of electrocardiographic changes. Approximately after 10 min of ischemia, the animals will start receiving a continuous 20 mL infusion of either vehicle or CsA (25 mg/kg); ischemia will be continued for an additional 20 min period after the start of treatment (i.e., 30 min total ischemic time). Subsequently (i.e., after 30 min of ischemia of which the last 20 min overlap with the treatment), the coronary snares will be released and the previously ischemic myocardium will be reperfused for up to 3 hrs. Treatment with either vehicle or CsA will be continued for 20 min into the reperfusion period. It should be noted that in sham-operated animals the vessel snares will be manipulated at the time of ischemia/reperfusion onset, but will not be either tightened or loosened.

Meanwhile, it also should be highlighted that in order to minimize any possible confounding effects on indices of myocardial injury, non self-resolving malignant arrhythmias/rhythms (e.g., ventricular tachycardia/fibrillation) developing during reperfusion will not be treated, and therefore, will be considered terminal (i.e., the experiment will be terminated prematurely).

Cardiovascular data collection will occur at 11 pre-determined time-points: post-instrumentation/stabilization (i.e., baseline), after 10 and 30 minutes of ischemia, as well as at 5, 15, 30, 60, 120, and 180 minutes post-reperfusion. Throughout the experiments, analog signals will be digitally sampled (1000 Hz) and recorded continuously with a data acquisition system (IOX; EMKA Technologies), and the following parameters will be determined at the above-mentioned time-points:

From bipolar transthoracic ECG (e.g., Lead II, aVF,): rhythm (arrhythmia quantification/classification), RR, PQ, QRS, QT, QTc, short-term QT instability, ST-segment deviation, and QT:TQ (restitution).

From solid-state manometer in aorta (Millar): arterial/aortic pressure (AoP).

From solid-state manometer in the LV (Millar): left-ventricular pressures (ESP, EDP) and derived indices (dP/dtmax, dP/dtmin, Vmax, and tau).

In addition, in order to determine/quantify the degree of irreversible myocardial injury (i.e., infarction) resulting from the I/R insult with and without CsA treatment cardiac biomarkers as well as infarct area will be evaluated.

Blood Samples.

Venous (<3 mL) whole blood samples will be collected for both pharmaco-kinetic (PK) analysis as well as for the evaluation of myocardial injury via cardiac biomarker analyses at six data-collection time-points: baseline, 30 min of ischemia, as well as 30, 60, 120 and 180 min post-reperfusion. Two clinically used biomarkers will be measured: cardiac Troponin-I (cTnI) and creatine-kinase (CK-MB). In addition, three arterial (~0.5 mL) whole blood samples will be collected at baseline, 30 min of ischemia, as well as the 60 and 180 min post-reperfusion for the determination of blood-gases; the arterial samples will be collected into blood gas syringes and used for the measurement of blood-gases via an I-Stat analyzer/cartridges (CG4+).

Venous blood will be drawn using pre-chilled syringes into pre-chilled tubes containing either K2EDTA (for PK analysis) or Serum-Separator (SST; for cardiac biomarkers), and then placed on wet ice pending centrifugation (for a maximum of 15 min). Samples will be centrifuged, plasma will be aliquoted (if possible) into 2 tubes each containing a minimum of 0.3 mL plasma/serum and frozen at approximately −70° C.

Histopathology/Histomorphometery.

At the completion of the protocol, irreversible myocardial injury (i.e., infarction) resulting from the I/R insult will be evaluated. In short, the coronary snares will be retightened and Evan's blue dye (1 mL/kg; Sigma, St. Louis, Mo.) will be injected intravenously to delineate the myocardial area-at-risk (AR) during ischemia. Approximately 5 min later, the heart will be arrested (by an injection of potassium chloride into the left atrium), and freshly excised. The LV will be sectioned perpendicular to its long axis (from apex to base) into 3 mm thick slices. The slices will be numbered consecutively, with "Slice #1" being the most apical. Subsequently, the slices will be incubated for 20 minutes in 2% triphenyl-tetrazolium-chloride (TTC) at 37° C. and fixed in a 10% non-buffered formalin solution (NBF).

Following fixation, the infarct and at-risks areas will be delineated/measured digitally. For such purpose, the thickness of each slice will be measured with a digital micrometer and later photographed/scanned. All photographs will be imported into an image analysis program (Image J; National Institutes of Health), and computer-assisted planimetry will be performed to determine the overall size of the infarct (I) and at-risk (AR) areas. For each slide, the AR (i.e., not stained blue) will be expressed as a percentage of the LV area, and the infarct size (I, not stained tissue) will be expressed as a percentage of the AR (I/AR). It should be noted, that, in all cases, quantitative histomorphometry will be performed by personnel blinded to the treatment assignment/study-design.

It is predicted that infarct size in the CsA-treated group will be significantly reduced compared to the control group. In particular, it is predicted that when the CsA is given prior to ischemia, there is a reduced hypoxic-induced mitochondrial dysfunction. These results will indicate that CsA administration prevents the occurrence of symptoms of acute cardiac ischemia-reperfusion injury. As such, CsA is useful in methods at preventing and treating ischemia-reperfusion injury in mammalian subjects.

Example 3. Effects of Combined Aromatic-Cationic Peptide and Cyclosporine Treatment in a Rabbit Model of Acute Myocardial Infarction Injury The combined effects of aromatic-cationic peptides or pharmaceutically acceptable salts thereof, such as acetate salt and trifluoroacetate salt, and cyclosporine in protecting against an acute myocardial infarction injury in a rabbit model are investigated. The myocardial protective effect of the peptide D-Arg-2'6'-Dmt-Lys-Phe-NH$_2$ and cyclosporine are demonstrated by this Example.

New Zealand white rabbits are used in this study. The rabbits are males and >10 weeks in age. Environmental controls in the animal rooms are set to maintain temperatures of 61° to 72° F. and relative humidity between 30% and 70%. Room temperature and humidity are recorded hourly, and monitored daily. There are approximately 10-15 air exchanges per hour in the animal rooms. Photoperiod is 12-hr light/12-hr dark (via fluorescent lighting) with exceptions as necessary to accommodate dosing and data collection. Routine daily observations are performed. Harlan Teklad, Certified Diet (2030C), rabbit diet is provided approximately 180 grams per day from arrival to the facility. In addition, fresh fruits and vegetables are given to the rabbits 3 times a week.

The peptide D-Arg-2'6'-Dmt-Lys-Phe-NH$_2$ (sterile lyophilized powder) and cyclosporine (Sandimmune, Novartis) are used as the test articles. Dosing solutions for the peptide are formulated at no more than 1 mg/ml, and are delivered via continuous infusion (IV) at a constant rate (e.g., 50 µL/kg/min). Cyclosporine is administered as a bolus injection of 2.5 mg of cyclosporine per kilogram of body weight or as a continuous infusion. Cyclosporine is dissolved in normal saline (final concentration, 25 mg per milliliter) and was injected through a catheter. Normal saline (0.9% NaCl) is used as a control.

The test/vehicle articles are given intravenously, under general anesthesia, in order to mimic the expected route of administration in the clinical setting of AMI and PTCA. Intravenous infusion are administered via a peripheral vein using a Kd Scientific infusion pump (Holliston, Mass. 01746) at a constant volume (e.g., 50 µL/kg/min). The study follows a predetermined placebo and sham controlled design. In short, 10-20 healthy, acclimatized, male rabbits are assigned to one of four study arms (approximately 2-10 animals per group). Arm A (n=4, CTRL/PLAC) includes animals treated with vehicle (vehicle; VEH, IV); Arm B (n=7, treated) includes animals treated with peptide and cyclosporine bolus; Arm C (n=7, treated) includes animals treated with peptide and cyclosporine IV infusion; Arm D (n=2, SHAM) includes sham-operated time-controls treated with vehicle (vehicle; VEH, IV) or peptide/cyclosporine.

In all cases, cardiovascular function is monitored both prior to and during ischemia, as well as for up to 180 min (3 h) post-reperfusion. The experiments are terminated 3 h post-reperfusion (end of study); irreversible myocardial injury (infarct size by histomorphometery) at this time-point is evaluated, and is the primary-end-point of the study.

Anesthesia/Surgical Preparation. General anesthesia is induced intramuscularly (IM) with a ketamine (~35-50 mg/kg)/xylazine (~5-10 mg/kg) mixture. A venous catheter is placed in a peripheral vein (e.g., ear) for the administration of anesthetics. In order to preserve autonomic function, anesthesia is maintained with continuous infusions of propofol (~8-30 mg/kg/hour) and ketamine (~1.2-2.4 mg/kg/hr). A cuffed tracheal tube is placed via a tracheotomy (ventral midline incision) and used to mechanically ventilate the lungs with a 95% O$_2$/5% CO$_2$ mixture via a volume-cycled animal ventilator (~40 breaths/minute with a tidal volume of ~12.5 ml/kg) in order to sustain PaCO$_2$ values broadly within the physiological range.

Once a surgical plane of anesthesia is reached, either transthoracic or needle electrodes forming two standard ECG leads (e.g., lead II, aVF, V2) are placed. A cervical cut-down exposes a carotid artery, which is isolated, dissected free from the surrounding tissue and cannulated with a dual-sensor high-fidelity micromanometer catheter (Millar Instruments); the tip of this catheter is advanced into the left-ventricle (LV) retrogradely across the aortic valve, in order to simultaneously determine aortic (root, proximal transducer) and left-ventricular (distal transducer) pressures. The carotid cut-down also exposes the jugular vein, which is cannulated with a hollow injection catheter (for blood sampling). Finally, an additional venous catheter is placed in a peripheral vein (e.g., ear) for the administration of vehicle/test articles.

Subsequently, the animals are placed in right-lateral recumbence and the heart is exposed via a midline thoracotomy and a pericardiotomy. The heart is suspended on a pericardial cradle in order to expose the left circumflex (LCX) and the left-anterior descending (LAD) coronary arteries. Silk ligatures are loosely placed (using a taper-point needle) around the proximal LAD and if necessary, depending on each animal's coronary anatomy, around one or more branches of the LCX marginal coronary arteries. Tightening

TABLE 10

Study Design.

| Group | Study Group | Ischemia Time | Reperfusion Time |
|---|---|---|---|
| A | CONTROL/PLACEBO | 30 Min (Last 20 Min. With Placebo; Bolus injection of placebo immediately prior to reperfusion) | 180 Min of Placebo |
| B | PEPTIDE + CsA BOLUS | 30 Min (Last 20 Min. With Peptide; Bolus injection of CsA immediately prior to reperfusion) | 180 Min of Peptide |
| C | PEPTIDE + CsA IV | 30 Min (Last 20 MM. With Peptide and CsA) | 180 Min of Peptide and CsA |
| D | SHAM (FOR SURGERY WITHOUT ISCHEMIA) | 0 Min (Last 20 Min. With Placebo; Bolus injection of placebo immediately prior to reperfusion) | 180 Min of Placebo (Vehicle) or Peptide |

In all cases, treatments are started approximately 30 min after the onset of a 30 min ischemic insult (coronary occlusion) and continued for up to 3 h following reperfusion.

of these snares (via small pieces of polyethylene tubing) allows rendering a portion of the left ventricular myocardium temporarily ischemic.

Once instrumentation is completed, hemodynamic stability and proper anesthesia depth are verified/ensured for at least 30 min. Subsequently, the animals are paralyzed with atracurium (~0.1 to 0.2 mg/kg/hr IV) in order to facilitate hemodynamic/respiratory stability. Following atracurium administration, signs of autonomic hyperactivity and/or changes in BIS values are used to evaluate anesthesia depth and/or to up-titrate the intravenous anesthetics.

Experimental Protocol/Cardiovascular Data Collection.

Immediately following surgical preparation, the animals are heparinized (100 units heparin/kg/h, IV bolus), and after hemodynamic stabilization (for approximately 30 min), baseline data are collected including venous blood for the evaluation of cardiac enzymes/biomarkers as well as of test-article concentrations.

Following hemodynamic stabilization and baseline measurements, the animals are subjected to an acute 60 min ischemic insult by tightening of the LAD/LCX coronary artery snares. Myocardial ischemia is visually confirmed by color (i.e., cyanotic) changes in distal distributions of the LAD/LCX and by the onset of electrocardiographic changes. Approximately after 10 min of ischemia, the animals receive a continuous infusion of either vehicle (saline), peptide or peptide+CsA; ischemia was continued for a additional 20 min (i.e., 30 min total) after the start of treatment. Subsequently (i.e., after 30 min of ischemia of which the last 20 min overlap with the treatment), the animals receive a bolus dose of CsA or vehicle, and the coronary snares are released. The previously ischemic myocardium is reperfused for up to 3 h. Treatment with either vehicle or peptide is continued throughout the reperfusion period. It should be noted that in sham-operated animals the vessel snares are manipulated at the time of ischemia/reperfusion onset, but are not either tightened or loosened.

Cardiovascular data collection occurs at 11 pre-determined time-points: post-instrumentation/stabilization (i.e., baseline), after 10 and 30 min of ischemia, as well as at 5, 15, 30, 60, 120, and 180 min post-reperfusion. Throughout the experiments, analog signals are digitally sampled (1000 Hz) and recorded continuously with a data acquisition system (IOX; EMKA Technologies), and the following parameters are determined at the above-mentioned time-points: (1) from bipolar transthoracic ECG (e.g., Lead II, aVF): rhythm (arrhythmia quantification/classification), RR, PQ, QRS, QT, QTc, short-term QT instability, and QT:TQ (restitution); (2) from solid-state manometer in aorta (Millar): arterial/aortic pressure (AoP); and (3) from solid-state manometer in the LV (Millar): left-ventricular pressures (ESP, EDP) and derived indices (dP/dtmax, dP/dtmin, Vmax, and tau). In addition, in order to determine/quantify the degree of irreversible myocardial injury (i.e., infarction) resulting from the FR insult with and without peptide treatment, cardiac biomarkers as well as infarct area are evaluated.

Blood Samples.

Venous (<3 mL) whole blood samples are collected for both pharmaco-kinetic (PK) analysis as well as for the evaluation of myocardial injury via cardiac biomarker analyses at six data-collection time-points: baseline, 30 min of ischemia, as well as 30, 60, 120 and 180 min post-reperfusion. Two clinically used biomarkers are measured: cardiac Troponin-I (cTnI) and creatine-kinase (CK-MB). In addition, three arterial (~0.5 mL) whole blood samples are collected at baseline, 60 min of ischemia, as well as the 60 and 180 min post-reperfusion for the determination of blood-gases; the arterial samples are collected into blood gas syringes and used for the measurement of blood-gases via an I-Stat analyzer/cartridges (CG4+).

Histopathology/Histomorphometry.

At the completion of the protocol, irreversible myocardial injury (i.e., infarction) resulting from the FR insult is evaluated. In short, the coronary snares are retightened and Evan's blue dye (1 mL/kg; Sigma, St. Louis, Mo.) was injected intravenously to delineate the myocardial area-at-risk (AR) during ischemia. Approximately 5 min later, the heart is arrested (by an injection of potassium chloride into the left atrium), and freshly excised. The LV is sectioned perpendicular to its long axis (from apex to base) into 3 mm thick slices. Subsequently, the slices are incubated for 20 min in 2% triphenyl-tetrazolium-chloride (TTC) at 37° C. and fixed in a 10% non-buffered formalin solution (NBF).

Following fixation, the infarct and at-risks areas are delineated/measured digitally. For such purpose, the thickness of each slice is measured with a digital micrometer and later photographed/scanned. All photographs are imported into an image analysis program (Image J; National Institutes of Health), and computer-assisted planometry is performed to determine the overall size of the infarct (I) and at-risk (AR) areas. For each slide, the AR (i.e., not stained blue) is expressed as a percentage of the LV area, and the infarct size (I, not stained tissue) is expressed as a percentage of the AR (I/AR). In all cases, quantitative histomorphometry is performed by personnel blinded to the treatment assignment/study-design.

Animal Observations.

Data are acquired on the EMKA's IOX system using ECG Auto software for analysis (EMKA Technologies). Measurements for all physiological parameters are made manually or automatically from (digital) oscillograph tracings. The mean value from 60 s of data from each targeted time point is used (if possible); however, as mentioned above, signals/tracing are recorded continuously throughout the experiments, in order to allow (if needed) more fine/detailed temporal data analysis (via amendments). Additional calculations are performed using Microsoft Excel. Data is presented as means with standard errors.

It is predicted that infarct size and apoptotic cell death in the peptide+CsA-treated groups will be significantly reduced compared to the control group. In particular, it is predicted that when the peptide+CsA is given prior to ischemia, there is a reduced hypoxic-induced mitochondrial dysfunction. These results will indicate that peptide administration prevents the occurrence of symptoms of acute cardiac ischemia-reperfusion injury. As such, aromatic-cationic peptides are useful in methods at preventing and treating ischemia-reperfusion injury in mammalian subjects.

Example 4. Effects of Combined Peptide and Cyclosporine Treatment in a Large Animal Model of Acute Myocardial Infarction Injury The effects of aromatic-cationic peptides or pharmaceutically acceptable salts thereof, such as acetate salt or trifluoroacetate salt, and cyclosporine in protecting against cardiac ischemia-reperfusion injury in a large animal model (e.g., a porcine or ovine model) are investigated. The myocardial protective effect of the D-Arg-2'6'-Dmt-Lys-Phe-NH$_2$.peptide and cyclosporine will be demonstrated by this Example.

General Surgical Protocol for Large Animal Models.

The animals are sedated with intramuscular ketamine (50 mg/kg), glycopyrrolate (0.2 mg/kg), and buprenorphine (0.05 mg/kg). After intubation, animals are ventilated with a mechanical respirator (Hallowell EMC Model AWS; Hallowell, Pittsfield, Mass.) using room air enriched with 0.6 L/min oxygen. Catheters are introduced into a small auricular artery and vein, and into the right jugular vein for the continuous measurement of blood pressure and the administration of intravenous medications. Anesthesia is maintained with an intravenous infusion of ketamine (0.02 to 0.04 mg/kg/min) and supplemental pentothal (2.5 to 5 mg/kg) as needed. Additionally, a pressure transducer (SPR-524; Millar Instruments, Houston, Tex.) is introduced through the right carotid artery into the left ventricle. Heart rate, blood pressure, surface electrocardiogram, and rectal temperature are continuously monitored (Hewlett Packard 78534C; Palo Alto, Calif.).

A left thoracotomy is performed, and a coronary snare is constructed by passing a suture around a large branch of the circumflex coronary artery at approximately 50% of the distance from base to apex of the heart, and threaded through a small piece of polyethylene tubing.

Alternate Surgical Protocol Using an Ovine Model.

Dorset male hybrid sheep weighing 35-40 kg are used in this study. Anesthesia is induced with thiopental sodium (10-15 mg/kg iv), and sheep are intubated, anesthetized with isoflurane (1.5-2%), and ventilated with oxygen (Drager anesthesia monitor, North American Drager, Telford, Pa.). Fluid-filled catheters are placed in a femoral artery and internal jugular vein for the continuous measurement of blood pressure and the administration of intravenous medications. A Swan-Ganz catheter (131h-7F, Baxter Healthcare, Irvine, Calif.) is introduced into the pulmonary artery through the internal jugular vein.

Animals undergo a left thoracotomy, and silicone vascular loops (Quest Medical, Allen, Tex.) are placed around the left anterior descending artery and its second diagonal branch, which is 40% of the distance from the apex to the base of the heart. Occlusion of these arteries at these locations produces a well-characterized model of anteroapical myocardial infarction. Arterial blood pressure, heart rate, surface electrocardiograms (ECG), and rectal temperature are continuously monitored (Hewlett Packard 78534C; Palo Alto, Calif.) throughout the protocol in all animals. A hyper/hypothermia unit (Medi-Therm III, Gaymar Industries, Orchard Park, N.Y.) is used to maintain core temperature of 39-40° C. in sheep. Arterial blood gases are measured in all animals, and the mean pH is maintained at 7.40±0.04 throughout the protocol.

Alternate Surgical Protocol Using a Porcine Model.

Anesthesia is induced in domestic pigs with thiopental sodium (10-15 mg/kg iv), and pigs are intubated, anesthetized with isoflurane (1.5-2%), and ventilated with oxygen (Drager anesthesia monitor, North American Drager, Telford, Pa.). Fluid-filled catheters are placed in a femoral artery and internal jugular vein for the continuous measurement of blood pressure and the administration of intravenous medications. A Swan-Ganz catheter (131h-7F, Baxter Healthcare, Irvine, Calif.) is introduced into the pulmonary artery through the internal jugular vein.

Animals undergo a left thoracotomy, and silicone vascular loops (Quest Medical, Allen, Tex.) are placed around the left anterior descending artery and its second diagonal branch, which is 40% of the distance from the apex to the base of the heart. Occlusion of these arteries at these locations produces a well-characterized model of anteroapical myocardial infarction. Arterial blood pressure, heart rate, surface electrocardiograms (ECG), and rectal temperature are continuously monitored (Hewlett Packard 78534C; Palo Alto, Calif.) throughout the protocol in all animals. A hyper/hypothermia unit (Medi-Therm III, Gaymar Industries, Orchard Park, N.Y.) is used to maintain core temperature of 39-40° C. in the pigs. Arterial blood gases are measured in all animals, and the mean pH is maintained at 7.40±0.04 throughout the protocol.

Treatment Groups.

In the case of the sheep or pig model, animals are divided into six groups, as shown in Table 7 below. The number of animals in each group may be from about 2 to about 15, suitably from about 4 to about 8 animals. After instrumentation, baseline hemodynamic data are recorded. Next, animals receive a 1-hour, continuous 20-mL infusion of either a phosphate buffered saline (PBS) vehicle (control) or peptide (low, mid, or high dose, and CsA). The peptide and CsA is dissolved in a vehicle.

Coronary snares are tightened to produce an ischemic region of the left ventricle. Ischemia is confirmed by a visible color change in the ischemic myocardial region, ST elevations on the electrocardiogram, and regional wall motion abnormalities on echocardiogram. At the end of the 20-120 min ischemic period (preferably 30-60 min) ischemic period, coronary snares are loosened and the previously ischemic myocardium is reperfused for 3 hours. Hemodynamic measurements are recorded throughout the reperfusion period. Each group receives continuous infusion of either a saline vehicle or peptide, as in the exemplary treatment groups shown in Table 11. Variations in the protocol design are contemplated by the present disclosure.

TABLE 11

| | | Treatment Groups | | | |
|---|---|---|---|---|---|
| | | ISCHEMIA PERIOD | | REPERFUSION PERIOD | |
| TREATMENT ARM | # OF ANIMALS | DURATION | INTERVENTION | DURATION | INTERVENTION |
| Placebo for Peptide/CsA | N = 2 | 0 | SHAM for surgery and ischemia Placebo for peptide administered as continuous infusion beginning at T + 40 min. and ongoing for 20 min. Placebo for CsA administered as bolus dose at T + 60 min. | 0 | SHAM with placebo for peptide cont. infusion for 180 min |

TABLE 11-continued

| | | Treatment Groups | | | |
|---|---|---|---|---|---|
| TREATMENT ARM | # OF ANIMALS | ISCHEMIA PERIOD | | REPERFUSION PERIOD | |
| | | DURATION | INTERVENTION | DURATION | INTERVENTION |
| Peptide/CsA (mid dose) | N = 2 | 0 | SHAM for surgery and ischemia Peptide administered as continuous infusion beginning at T + 40 min. and ongoing for 20 min. CsA administered as bolus dose at T + 60 min. | 0 | SHAM with peptide cont. infusion for 180 min |
| Placebo for Peptide/CsA | N = 8 | 60 min | Placebo for peptide administered as continuous infusion beginning at T + 40 min. and ongoing for 20 min. Placebo for CsA administered as bolus dose at T + 60 min. | 180 min | Placebo for peptide cont. infusion for 180 min |
| Peptide (lowdose)/CsA | N = 8 | 60 min | Placebo for peptide administered as continuous infusion beginning at T + 40 min. and ongoing for 20 min. CsA administered as bolus dose at T + 60 min. | 180 min | Peptide cont. infusion for 180 min |
| Peptide (middose)/CsA | N = 8 | 60 min | Placebo for peptide administered as continuous infusion beginning at T + 40 min. and ongoing for 20 min. CsA administered as bolus dose at T + 60 min. | 180 min | Peptide cont. infusion for 180 min |
| Peptide (high dose)/CsA | N = 8 | 60 min | Placebo for peptide administered as continuous infusion beginning at T + 40 min. and ongoing for 20 min. CsA administered as bolus dose at T + 60 min. | 180 min | Peptide cont. infusion for 180 min |

Temperature and Hemodynamic Measurements.

Arterial blood pressure, left ventricular pressure, heart rate, surface electrocardiogram, and rectal temperature are continuously monitored throughout the protocol in all animals. Hemodynamic, heart rate, and temperature measurements are recorded at baseline, after initiation of peptide or placebo for peptide infusion, at 40 min of ischemia, immediately prior to and after the release of the coronary snares, and after 3 hours of reperfusion. The rate pressure product is calculated by multiplying the heart rate by the systolic blood pressure at all time points.

Analysis of Areas at Risk and Infarct Size.

At the completion of the protocol, the coronary snares are retightened; vascular clamps are used to occlude the aorta, pulmonary artery, and inferior vena cava; and the right atrium is incised. One milliliter per kilogram of Evans blue dye (Sigma, St. Louis, Mo.) is injected via the left atrium to delineate the ischemic myocardial risk area (AR).

All animals are euthanized via an injection of potassium chloride into the left atrium. Next, the heart is excised, and the LV is sectioned perpendicular to its long axis into six slices. The thickness of each slice is measured with a digital micrometer, and all slices are photographed. All slices are then incubated in 2% triphenyltetrazolium chloride (TTC) at 37° C. for 20 min and rephotographed. All photographs are imported into an image analysis program (Image Pro Plus, Media Cybernetics, Silver Spring, Md.). Myocardium unstained by Evans blue dye is determined to be the AR.

Infarct area is determined by incubating the myocardium in TTC. TTC is a colorless dye, which is reduced to a brick-red colored precipitate in the presence of the coenzyme NADH. During reperfusion of previously ischemic myocardium, NADH is washed out of all necrotic myocytes. This results in a clear delineation of viable myocardium, which stains brick-red, and non-viable myocardium, which is visualized as an unstained, pale color. See, e.g., Leshnower et al., *Am J Physiol Heart Circ Physiol* 293: H1799-H1804, 2007, for exemplary images.

Computerized planimetry (Image Pro Plus, Media Cybernetics) is used to measure AR and infarct areas. AR is expressed as a percentage of the LV (AR/LV), and infarct size is expressed as a percentage of the AR (I/AR). AR and FAR are measured for the all slices, and a total AR and I/AR for the entire LV is calculated.

Tissue Preparation.

The entire AR from LV slices are excised. A 1- to 2-mm transmural specimen is removed from the AR, snap frozen in liquid nitrogen, and stored at −80° C. The remainder of the AR is fixed for 24 hours in 10% formalin and subsequently embedded in paraffin.

In Situ Oligo Ligation Assay.

For the identification of apoptotic cells, an in situ oligo ligation (ISOL) assay (Intergen 7200; Intergen, Purchase, N.Y.) with a high specificity for staining the specific DNA fragmentation characteristic of apoptosis is selected. This assay utilizes T4 DNA ligase to bind synthetic biotinylated oligonucleotides to 3'-dT overhangs. Paraffin-embedded tissue is sectioned into 5-μm slices and deparaffinized by three changes of xylene, followed by three changes of absolute ethanol. Subsequently, endogenous peroxidase is quenched in 3% hydrogen peroxide in PBS. After washing the tissue sections, they are treated with 20 μg/mL proteinase K in PBS, washed again, and placed in an equilibration buffer. Next, a solution of T4 DNA ligase and oligonucleotides is applied to the slides and incubated overnight at 16° to 22° C. ApopTag detection of ligated oligonucleotides is accomplished by applying a streptavidin-peroxidase conjugate that is developed with diaminobenzidine. Finally, tissue sections are counterstained in hematoxylin.

Entire tissue sections are digitalized using a scanning microscope and analyzed using an image analysis software package (Image Pro Plus; MediaCybernetics, Silver Spring, Md.). ISOL-positive and ISOL-negative nuclei are counted in the AR. Results are expressed as an apoptic index, which is defined as the percentage of ISOL positive cells per total number of cells in the entire AR.

Transmurality Analysis.

Using advanced planimetry techniques (Image Pro Plus, MediaCybernetics), a transmural analysis is performed on the AR in the second slice from the apex to evaluate the spread of ischemic cell death within different regions of the myocardium. The second slice is selected because of its consistent appearance following ischemia and reperfusion from prior experiments. After basic planimetry is completed, the radius of the left ventricular wall is divided into three equivalent lengths at multiple points around the circumference, and individual arcs are created, which connected these radial points. Next, these arcs are connected circumferentially to form concentric ellipses, which divide the AR into three statistically equivalent areas (subendocardium, midmyocardium, and subepicardium; P=0.05). AR and I/AR are measured.

Myocardial Fluorescence Spectroscopy.

Fluorescence spectroscopy of animal myocardium is conducted with a fluorometer. This fluorometer is a mobile optical-electrical apparatus that collects fluorescence signals of any type of tissue through a 3-mm-tip light guide catheter. The incident light is a broadband mercury arc lamp that can be filtered at two pairs of excitation/emission wavelengths by an air turbine filter wheel rotating at 50 Hz. Consequently, up to four signals can be multiplexed to a photo detector in order to make four-wavelength channel optical measurements of tissue metabolism. In this experiment two channels are used for excitation and the other two for emission signals. The light intensity that is incident on tissue at the fiber tip is 3 μW/mm². In cardiac fluorometry experiments, the excitation wavelengths of FAD and NADH are obtained by filtering the resonance lines of the mercury arc lamp at 436 nm and 366 nm by band-pass filters 440DF20 and 365HT25, respectively. The fluorescence intensities are then detected by a photomultiplier tube, converted to an electric voltage, digitized and displayed. Specific instrument specifications are kept the same for all the experiments.

The fluorometer catheter is placed on the epicardial surface in the center of the anticipated region of ischemia and continuous recording of the fluorescence signals for FAD and NADH signals is performed during 10 min of baseline, 60 min of infusion of saline or peptide, 30 min of ischemia, and 180 min of reperfusion. The redox ratio is calculated as $FAD_f/(FAD_f+NAD_f)$ every five minutes from the continuously recorded FAD and NAD. The redox ratio (RR) in each group are averaged and expressed as mean±standard error at five-minute time points for statistical analysis and ten-minute intervals for spectroscopic graphs.

Regional Blood Flow Measurements.

In test subjects, approximately fifteen million color-coded, 15.5 μm-diameter NuFlow Fluorescent microspheres (IMT Laboratories, Irvine, Calif.) are injected to measure the degree of ischemia during coronary occlusion and to study the effects of increasing ischemic time on microvascular integrity after reperfusion. Injections are made at baseline, after 30 min of ischemia, at the onset of reperfusion, and after 180 min of reperfusion. Reference blood samples are taken at all time points. At the end of the experiment, in a similar fashion to the transmural analysis described above, the AR from the second slice from the apex in each animal is isolated and circumferentially sectioned into three equivalent areas: subendocardium, midmyocardium, and subepicardium. The three different areas of myocardium and reference blood samples are analyzed using flow cytometry for microsphere content by IMT Laboratories. Regional perfusion is calculated using the following formula: $Q_m=(C_m \times Q_r)/C_r$, where $Q_m$ is myocardial blood flow per gram ml min$^{-1}$ g$^{-1}$) of sample; $C_m$ is microsphere count per gram of tissue in sample; $Q_r$ is withdrawal rate of the reference blood sample ml/min); and $C_r$ is microsphere count in the reference blood sample. Regional blood flow (RBF) values are normalized and expressed as a percentage of baseline flow.

Analysis of Mitochondrial Disruption.

Three random tissue sections from the infarct region are embedded in EPON. One section is cut, stained, and analyzed, while the remaining two sections are archived for future analysis. Fifty mitochondria from all regions of the sample are assessed at a standardized magnification. The number of mitochondria with disrupted outer membranes are tallied and the percentage of disrupted mitochondria will be reported.

Transmission Electron Microscopy.

Myocardial punch biopsies are obtained from the AR from 2 animals from each of the control and peptide groups. Tissue is also obtained from 4 normal animals that are not subjected to the ischemia/reperfusion protocol. Biopsies are preserved in fixative (2.5% glutaraldehyde, 2.0% paraformaldehyde, 0.1 M sodium cacodylate [NaCaC]) for 24 hours at 4° C. After several washes in 0.1M NaCaC, samples are post-fixed with buffered 2% osmium tetroxide for 1 hour at 4° C. Subsequent washes in 0.1M NaCaC, water, and 2% aqueous uranyl acetate are used to destain samples. Tissue samples are dehydrated in serial washes of ethanol and propylene oxide, before a slow infiltration with EPON 812. Samples are cured at 70° C. for 48 hours and cut, stained, and imaged on a Jeol-10-10 transmission electron microscope (Jeol, Akishima, Japan). Random images are captured from each sample for comparative analysis. To assess the degree of mitochondrial disruption, five random images of mitochondria at 12,000 magnification per pig or sheep are captured from each specimen. Morphologic differences in mitochondria are assessed in the nuclear cap, a region surrounding the cell nucleus. The total number of mitochondria and the number of disrupted mitochondria are counted and averaged. The mean percentage of disrupted mitochondria is calculated and reported for each group.

The endpoints set forth in Table 12 will be measured using an appropriate technique known in the art, such as the exemplary techniques described in the preceding paragraphs.

TABLE 12

Experimental Endpoints.

| Study Parameter to be Assessed | Pre-Ischemic Period | Ischemic Period | Immediately Post-Ischemia | Short Term to Longer Term Post-Ischemia | At End of Reperfusion Period | At Post-Mortem |
|---|---|---|---|---|---|---|
| Cardiovascular Hemodynamics | X | X | X | X | X | |
| ECG Waveforms and Intervals | X | X | X | X | X | |
| Regional LV Wall Thickening | X | X | X | X | X | |
| Mitochondrial Function (REDOX State) | X | X | X | X | X | |
| Mitochondrial Structure | | | | | | X |
| Assessment of Apoptosis | | | | | | X |
| LV Infarct Size, (AR/LV, IA/LV, IA/AR) | | | | | | X |

It is predicted that infarct size and apoptotic cell death in the peptide+CsA-treated groups will be significantly reduced compared to the control group. It is also predicted that transmission electron microscopy will reveal a preservation of normal mitochondria morphology and a reduction in the percentage of disrupted mitochondria in the peptide+CsA-treated group compared with the control group.

It is also predicted that the peptide+CsA will influence mitochondrial function during both ischemia and reperfusion as indicated by the time course curves of the redox ratio (RR). The RR is calculated using intrinsic NAD and FAD fluorescence measurements is a sensitive index of mitochondrial metabolism. Since the fluorescence of NAD and FAD vary inversely with mitochondrial redox state the RR ($FAD_f/(FAD_f+NAD_f)$) has been found to correlate more strongly with mitochondrial function than either of the individual fluorescent measurements alone. In particular, it is predicted that when the peptide is given prior to ischemia, there is a reduced hypoxic-induced mitochondrial dysfunction indicated by a blunted drop in the RR during ischemia. Likewise, the RR is not expected to rise as quickly upon reperfusion the peptide+CsA-treated groups as compared to the control groups.

These results will indicate that peptide and CsA administration prevents the occurrence of symptoms of acute cardiac ischemia-reperfusion injury. As such, the combination of cyclosporine and aromatic-cationic peptides are useful in methods at preventing and treating ischemia-reperfusion injury in mammalian subjects.

Example 5. Effects of Combined Peptide and Cyclosporine Treatment in Humans with Acute Myocardial Infarction Injury This Example will determine whether the administration of an aromatic-cationic peptide, or a pharmaceutically acceptable salt thereof such as acetate salt or trifluoroacetate salt and cyclosporine at the time of revascularization would limit the size of the infarct during acute myocardial infarction. In this example, the aromatic-cationic peptide D-Arg-2'6'-Dmt-Lys-Phe-NH$_2$ is used.

Study group.

Men and women, 18 years of age or older, who present within 6 hours after the onset of chest pain, who have ST-segment elevation of more than 0.1 mV in two contiguous leads, and for whom the clinical decision is made to treat with percutaneous coronary intervention (PCI) are eligible for enrollment. Patients are eligible for the study whether they are undergoing primary PCI or rescue PCI. Occlusion of the culprit coronary artery (Thrombolysis in Myocardial Infarction [TIMI] flow grade 0) at the time of admission is also a criterion for inclusion.

Angiography and Revascularization.

Left ventricular and coronary angiography is performed with the use of standard techniques, just before revascularization. Revascularization is performed by PCI with the use of direct stenting. Alternative revascularization procedures include, but are not limited to, balloon angioplasty; insertion of a bypass graft; percutaneous transluminal coronary angioplasty; and directional coronary atherectomy Experimental Protocol.

After coronary angiography is performed but before the stent is implanted, patients who meet the enrollment criteria are randomly assigned to either the control group or the peptide group. Randomization is performed with the use of a computer-generated randomization sequence. Less than 10 min before direct stenting, the patients in the peptide group receive an intravenous bolus injection of D-Arg-2'6'-Dmt-Lys-Phe-NH$_2$ and cyclosporine. The peptide is dissolved in normal saline (final concentration, 25 mg per milliliter) and is injected through a catheter that is positioned within an antecubital vein. Either separately or simultaneously, cyclosporine (final concentration, 25 mg per milliliter) is injected through the catheter. Normal saline (0.9% NaCl) was used as a control. The patients in the control group receive an equivalent volume of normal saline.

Infarct Size.

The primary end point is the size of the infarct as assessed by measurements of cardiac biomarkers. Blood samples are obtained at admission and repeatedly over the next 3 days. The area under the curve (AUC) (expressed in arbitrary units) for creatine kinase and troponin I release (Beckman kit) is measured in each patient by computerized planimetry. The principal secondary end point is the size of the infarct as measured by the area of delayed hyperenhancement that is seen on cardiac magnetic resonance imaging (MM), assessed on day 5 after infarction. For the late-enhancement analysis, 0.2 mmol of gadolinium—tetrazacyclododecanetetraacetic acid (DOTA) per kilogram is injected at a rate of 4 ml per second and was flushed with 15 ml of saline.

Delayed hyperenhancement is evaluated 10 min after the injection of gadolinium—DOTA with the use of a three-dimensional inversion-recovery gradient—echo sequence. The images are analyzed in shortaxis slices covering the entire left ventricle.

Myocardial infarction is identified by delayed hyperenhancement within the myocardium, defined quantitatively by an intensity of the myocardial postcontrast signal that is more than 2 SD above that in a reference region of remote, noninfarcted myocardium within the same slice. For all slices, the absolute mass of the infracted area is calculated according to the following formula: infarct mass (in grams of tissue)=E (hyperenhanced area [in square centimeters])×slice thickness (in centimeters)×myocardial specific density (1.05 g per cubic centimeter).

Other End Points.

The whole-blood concentration of peptide is immediately prior to PCI as well as at 1, 2, 4, 8 and 12 hours post PCI. Blood pressure and serum concentrations of creatinine and potassium are measured on admission and 24, 48, and 72 hours after PCI. Serum concentrations of bilirubin, γ-glutamyltransferase, and alkaline phosphatase, as well as white-cell counts, are measured on admission and 24 hours after PCI.

The cumulative incidence of major adverse events that occur within the first 48 hours after reperfusion are recorded, including death, heart failure, acute myocardial infarction, stroke, recurrent ischemia, the need for repeat revascularization, renal or hepatic insufficiency, vascular complications, and bleeding. The infarct-related adverse events are assessed, including heart failure and ventricular fibrillation. In addition, 3 months after acute myocardial infarction, cardiac events are recorded, and global left ventricular function is assessed by echocardiography (Vivid 7 systems; GE Vingmed).

It is predicted that administration of the peptide and cyclosporine at the time of reperfusion will be associated with a smaller infarct by some measures than that seen with placebo.

Example 6: Effects of Combined Peptide and Cyclosporine Treatment on Organ Preservation For heart transplantation, the donor heart is preserved in a cardioplegic solution during transport. The preservation solution contains high potassium which effectively stops the heart from beating and conserves energy. However, the survival time of the isolated heart is still quite limited.

This example demonstrates the effects of aromatic-cationic peptides, or a pharmaceutically acceptable salt thereof, such as acetate salt or trifluoroacetate salt, and cyclosporine on organ preservation. The protective effect of administering D-Arg-2'6'-Dmt-Lys-Phe-NH$_2$ and cyclosporine on mammalian organ survival following prolonged ischemia is demonstrated.

Experimental Protocol.

Isolated guinea pig hearts are perfused in a retrograde fashion with an oxygenated Krebs-Henseleit solution at 34° C. After 30 min. of stabilization, the hearts are perfused with a cardioplegic solution CPS (St. Tohomas) with or without D-Arg-2'6'-Dmt-Lys-Phe-NH$_2$ and cyclosporine for 3 min. Global ischemia is then induced by complete interruption of coronary perfusion for 90 min. Reperfusion is subsequently carried out for 60 min. with oxygenated Krebs-Henseleit solution. Contractile force, heart rate and coronary flow are monitored continuously throughout the experiment.

Conclusions:

It is predicted that administration of the peptide and cyclosporine will have a protective effect on organ survival after prolonged ischemia compared to controls.

Example 7: Effects of Combined Peptide and Cyclosporine Treatment on Nephrotoxicity in Transplant Patients To prevent organ or tissue rejection after transplant, patients often receive a regimen of the immunosuppressive drug cyclosporine. Cyclosporine levels are established and maintained in the subject at levels to effectively suppress the immune system. However, nephrotoxicity is a concern for these subjects, and the level of the drug in the subject's blood is monitored carefully. Cyclosporine doses are adjusted accordingly in order to not only prevent rejection, but also to deter these potentially damaging side effects. Typically, an adult transplant patient receives cyclosporine as follows: IV: 2 to 4 mg/kg/day IV infusion once a day over 4 to 6 hours, or 1 to 2 mg/kg IV infusion twice a day over 4 to 6 hours, or 2 to 4 mg/kg/day as a continuous IV infusion over 24 hours. Capsules: 8 to 12 mg/kg/day orally in 2 divided doses. Solution: 8 to 12 mg/kg orally once a day. In some patients, doses can be titrated downward with time to maintenance doses as low as 3 to 5 mg/kg/day. In some patients, the tolerance for cyclosporine is poor, and cyclosporine therapy must be discontinued, the dosage lowered, or the dosage regimen cycled so as to prevent destruction of the subject's kidney.

This example demonstrates the effects of aromatic-cationic peptides, or a pharmaceutically acceptable salt thereof, such as acetate salt or trifluoroacetate salt, and cyclosporine on post-transplant organ health (e.g., ischemia-reperfusion injury post transplant and organ rejection), as well as kidney health (e.g., nephrotoxic effects of cyclosporine). The protective effect of administering an aromatic-cationic peptide such as D-Arg-2'6'-Dmt-Lys-Phe-NH$_2$ on the transplant organ or tissue, and on kidney health during cyclosporine treatment is demonstrated.

Transplant subjects receiving cyclosporine pursuant to standard pre- and post-transplant procedures are divided into seven groups as follows:

TABLE 13

Transplant subject peptide and cyclosporine regimen

| Subject Group | Cyclosporine | Peptide received | | |
|---|---|---|---|---|
| | | Before transplant | During transplant | After transplant |
| 1 | + | − | − | − |
| 2 | + | + | − | − |
| 3 | + | − | + | − |
| 4 | + | − | − | + |
| 5 | + | + | + | − |
| 6 | + | − | + | + |
| 7 | + | + | + | + |

A therapeutically effective amount of an aromatic-cationic peptide or pharmaceutically acceptable salt thereof such as acetate or trifluoroacetate salt is administered to subjects prior to, during and/or after transplant as show in Table 13 above. Subjects are monitored for health and function of the transplanted tissue or organ, as well as the incidence and severity of nephrotoxicitity often seen with prolonged cyclosporine administration.

Conclusions:

It is predicted that subjects who receive the peptide will have a healthier transplanted organ or tissue, and/or will be able to maintain a higher and/or more consistent cyclosporine dosage for longer periods of time compared to subjects who do not receive the peptide.

EQUIVALENTS

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatuses within the scope of the invention, in addition to those enumerated herein, will be apparent to those skilled in the art from the foregoing descriptions. Such modifications and variations are intended to fall within the scope of the appended claims. The present invention is to be limited only by the terms of the appended claims, along with the full scope of equivalents to which such claims are entitled. It is to be understood that this invention is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

Other embodiments are set forth within the following claims.

What is claimed is:

1. A method for treating ischemia and/or reperfusion injury in a subject in need thereof, the method comprising administering simultaneously, separately or sequentially an effective amount of (i) an aromatic-cationic peptide or a pharmaceutically acceptable salt thereof, wherein the aromatic-cationic peptide is selected from the group consisting of: Tyr-D-Arg-Phe-Lys-NH$_2$; 2',6'-Dmt-D-Arg-Phe-Lys-NH$_2$, Phe-D-Arg-Phe-Lys-NH$_2$; 2',6'-Dmp-D-Arg-Phe-Lys-NH$_2$; and D-Arg-2',6'-Dmt-Lys-Phe-NH$_2$ and (ii) an additional active agent comprising a functional analogue of cyclosporine.

2. The method of claim 1, wherein the pharmaceutically acceptable salt comprises acetate salt or trifluoroacetate salt.

3. The method of claim 1, wherein the aromatic-cationic peptide comprises D-Arg-2'6'-Dmt-Lys-Phe-NH$_2$ or a pharmaceutically acceptable salt thereof selected from acetate salt or trifluoroacetate salt.

4. A pharmaceutical composition comprising (i) an aromatic-cationic peptide or a pharmaceutically acceptable salt thereof, wherein the aromatic-cationic peptide is selected from the group consisting of: Tyr-D-Arg-Phe-Lys-NH$_2$; 2',6'-Dmt-D-Arg-Phe-Lys-NH$_2$, Phe-D-Arg-Phe-Lys-NH$_2$; 2',6'-Dmp-D-Arg-Phe-Lys-NH$_2$; and D-Arg-2',6'-Dmt-Lys-Phe-NH$_2$, and (ii) an additional active agent comprising a functional analogue of cyclosporine.

5. The pharmaceutical composition of claim 4, wherein the pharmaceutically acceptable salt comprises acetate salt or trifluoroacetate salt.

6. The pharmaceutical composition of claim 5, wherein the aromatic-cationic peptide comprises D-Arg-2'6'-Dmt-Lys-Phe-NH$_2$ or a pharmaceutically acceptable salt thereof, selected from acetate salt and trifluoroacetate salt.

7. A composition comprising: an (i) an aromatic-cationic peptide or a pharmaceutically acceptable salt thereof, wherein the aromatic-cationic peptide is selected from the group consisting of: Tyr-D-Arg-Phe-Lys-NH$_2$; 2',6'-Dmt-D-Arg-Phe-Lys-Nth; Phe-D-Arg-Phe-Lys-NH$_2$; 2',6'-Dmp-D-Arg-Phe-Lys-NH$_2$; and D-Arg-2',6'-Dmt-Lys-Phe-NH$_2$, and (ii) an additional active agent comprising a functional analogue of cyclosporine, wherein the aromatic-cationic peptide is linked to the additional active agent by a linker.

8. The composition of claim 7, wherein the pharmaceutically acceptable salt comprises acetate salt or trifluoroacetate salt.

9. The composition of claim 8, wherein the aromatic-cationic peptide comprises D-Arg-2',6'-Dmt-Lys-Phe-NH$_2$ or a pharmaceutically acceptable salt thereof selected from acetate salt or trifluoroacetate salt, and wherein the linker comprises an enzyme-cleavable linker.

10. The method of claim 1, wherein the aromatic-cationic peptide is administered intravenously, intradermally, intraperitoneally, subcutaneously, orally, transdermally, topically, intraocularly, iontophoretically, transmucosally, or by inhalation.

11. The method of claim 1, wherein the ischemia and/or reperfusion injury comprises vessel occlusion injury or cardiac ischemia-reperfusion injury.

12. The pharmaceutical composition of claim 5, wherein the aromatic-cationic peptide is formulated to be administered intravenously, intradermally, intraperitoneally, subcutaneously, orally, transdermally, topically, intraocularly, iontophoretically, transmucosally, or by inhalation.

13. The composition of claim 8, wherein the aromatic-cationic peptide is formulated to be administered intravenously, intradermally, intraperitoneally, subcutaneously, orally, transdermally, topically, intraocularly, iontophoretically, transmucosally, or by inhalation.

14. The composition of claim 8, wherein the aromatic-cationic peptide comprises D-Arg-2',6'-Dmt-Lys-Phe-NH$_2$ or a pharmaceutically acceptable salt thereof selected from acetate salt and trifluoroacetate salt, and wherein the linker comprises a pH-sensitive linker.

* * * * *